(12) United States Patent
Nagashima et al.

(10) Patent No.: US 11,773,052 B2
(45) Date of Patent: Oct. 3, 2023

(54) ENAMINE COMPOUND AND USE THEREOF

(71) Applicant: JAPAN SCIENCE AND TECHNOLOGY AGENCY, Kawaguchi (JP)

(72) Inventors: Hideo Nagashima, Kasuga (JP); Atsushi Tahara, Kasuga (JP); Ikumi Kitahara, Kasuga (JP); Yoichiro Kuninobu, Kasuga (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 0 days.

(21) Appl. No.: 16/489,563

(22) PCT Filed: Mar. 2, 2018

(86) PCT No.: PCT/JP2018/008116
§ 371 (c)(1),
(2) Date: Oct. 22, 2019

(87) PCT Pub. No.: WO2018/159834
PCT Pub. Date: Sep. 7, 2018

(65) Prior Publication Data
US 2020/0087245 A1 Mar. 19, 2020

(30) Foreign Application Priority Data

Mar. 2, 2017 (JP) .................................. 2017-039057

(51) Int. Cl.
C07C 211/55 (2006.01)
C07C 255/58 (2006.01)
C07D 265/38 (2006.01)
C07D 285/14 (2006.01)
C07F 5/02 (2006.01)
C09K 11/06 (2006.01)

(52) U.S. Cl.
CPC .......... C07C 211/55 (2013.01); C07C 255/58 (2013.01); C07D 265/38 (2013.01); C07D 285/14 (2013.01); C07F 5/02 (2013.01); C09K 11/06 (2013.01)

(58) Field of Classification Search
CPC ................ C07C 211/55; C07C 255/58; C07D 285/14; C07D 265/38
USPC ........................................................ 544/102
See application file for complete search history.

(56) References Cited

U.S. PATENT DOCUMENTS

2002/0192670 A1  12/2002  Tokunaga et al.

FOREIGN PATENT DOCUMENTS

| EP | 866645 A1 * | 9/1998 | ......... H01L 51/5012 |
|---|---|---|---|
| JP | 2-24663 A | 1/1990 | |
| JP | 04324449 A * | 11/1992 | |
| JP | 6-73058 A | 3/1994 | |
| JP | 2000-239238 A | 9/2000 | |
| JP | 2002-82458 A | 3/2002 | |
| JP | 2002-327130 A | 11/2002 | |
| JP | 2006-269834 A | 10/2006 | |
| JP | 2010-65069 A | 3/2010 | |
| JP | 2010-126571 A | 6/2010 | |
| JP | 2012-144447 A | 8/2012 | |
| JP | 2013-193957 A | 9/2013 | |
| JP | 2014-2413 A | 1/2014 | |
| JP | 2018-20976 | 2/2018 | |
| JP | 2018020976 A * | 2/2018 | |

(Continued)

OTHER PUBLICATIONS

Hanley et al. Journal of the American Chemical Society (2011), 133(39), 15661-15673.*
International Search Report dated May 29, 2018 in PCT/JP2018/008116 filed Mar. 2, 2018.
Hanley, P. S. et al., "Intermolecular Migratory Insertion of Unactivated Olefins into Palladium-Nitrogen Bonds. Steric and Electronic Effects on the Rate of Migratory Insertion", Journal of the American Chemical Society, vol. 133, No. 39, 2011, pp. 15661-15673.

(Continued)

*Primary Examiner* — Kahsay Habte
(74) *Attorney, Agent, or Firm* — Oblon, McClelland, Maier & Neustadt, L.L.P.

(57) ABSTRACT

Provided are a donor-acceptor type compound having a novel structure and its use.
An enamine compound represented by general formula (1)

$$R^1-A-\underset{\underset{R^2}{|}}{C}=CH-N\underset{R^4}{\overset{R^3}{\diagup}} \quad (1)$$

(in the formula:
$R^1$ represents an electron-withdrawing group;
A represents a divalent aromatic hydrocarbon group which may contain a substituent, a divalent aromatic heterocyclic group which may contain a substituent or a divalent unsaturated aliphatic hydrocarbon group which may contain a substituent;
$R^2$ represents a hydrogen atom or a hydrocarbon group which may contain a substituent;
$R^3$ and $R^4$ are the same or different from each other and represent an aromatic hydrocarbon group which may contain a substituent or an aromatic heterocyclic group which may contain a substituent, or $R^3$ and $R^4$ together form an optionally substituted bicyclic aromatic heterocyclic group containing two or more nitrogen atoms or a nitrogen atom and an oxygen atom or a sulfur atom, or a tricyclic aromatic heterocyclic group which may contain a substituent; and $R^2$ and A, or $R^2$ and $R^3$ may together form a cyclic structure).

21 Claims, 5 Drawing Sheets

(56) References Cited

FOREIGN PATENT DOCUMENTS

| KR | 2015108209 A | * | 9/2015 | ............ C07C 211/54 |
| KR | 10-2016-0077736 A | | 7/2016 | |

OTHER PUBLICATIONS

He, Q. et at., "Synthesis, crystal structure and spectroscopic properties of an unsymmetrical compound with carbazole and benzothiadiazole units", Tetrahedron Letters, vol. 48, No. 24, 2007, pp. 4249-4253.

Prukała, W. et al., "Highly stereoselective synthesis of para-substituted (E)-N-styrylcarbazoles via sequential silylative coupling—Hiyama coupling reaction", Tetrahedron, vol. 63, No. 5, 2007, pp. 1107-1115.

Office Action issued in Chinese Patent Application No. 201880014759. 1, dated Dec. 6, 2021, w/English Translation.

Japanese Office Action dated Nov. 22, 2022 in Japan Patent Application No. 2019-503156 (with unedited computer-generated English translation), 9 pages.

Hou et al., "A rigid conjugated pyridinylthiazole derivative and its nanoparticles for divalent copper fluorescent sensing in aqueous media", Tetrahedron Letters, vol. 52, Issue 21, 2011, pp. 2710-2714.

Johnsen et al., "Effects of conjugation length and resonance enhancement on two-photon absorption in phenylene-vinylene oligomers", Physical Chemistry Chemical Physics, vol. 10, 2008, pp. 1177-1191.

Korean Office Action dated Sep. 23, 2022 for Korean Patent Application No. 10-2019-7025806 (with unedited computer generated English translation), 21 pages.

CAS RN 77475-25-3.
CAS RN 77475-27-5.
CAS RN 77475-29-7.

Dempsey, G.T., et al., "Photoswitching Mechanism of Cyanine Dyes", J. Am. Chem. Soc. 2009, vol. 131, pp. 18192-18193 (Dec. 4, 2009).

Ma, X., et al., "A high-efficiency cyanine dye for dye-sensitized solar cells", Tetrahedron 2008, vol. 64, pp. 345-350 (Jan. 7, 2008).

Motoyama, Y., et al., "Highly efficient synthesis of aldenamines from carboxamides by iridium-catalyzed silane-reduction/dehydration under mild conditions", Chem. Commun., 2009, pp. 1574-1576 (Feb. 2, 2009).

Yukihiro Motoyama et al., "Highly efficient synthesis of aldenamines from carboxamides by iridium-catalyzed silane reduction/dehydration under mild conditions", Chem. Commun., 2009, pp. 1574-1576.

Atsushi Tahara et al., "Catalyst Design of Vaska-Type Iridium Complexes for Highly Efficient Synthesis of π-Conjugated Enamines", Organometallics, 2015, 34, pp. 4895-4907.

* cited by examiner

[Fig. 1]
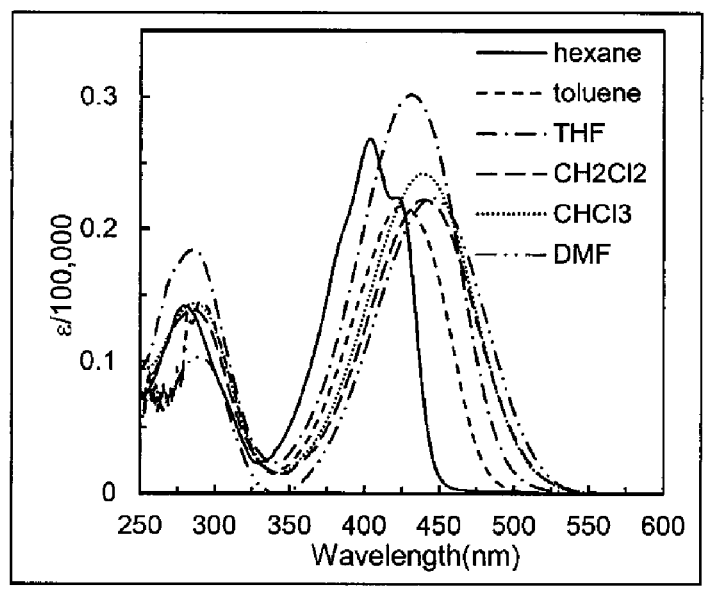
[Fig. 2]
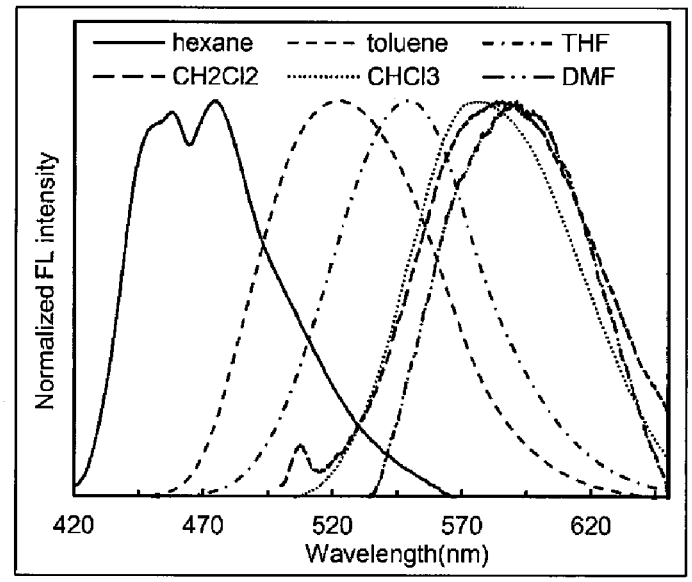

[Fig. 3]
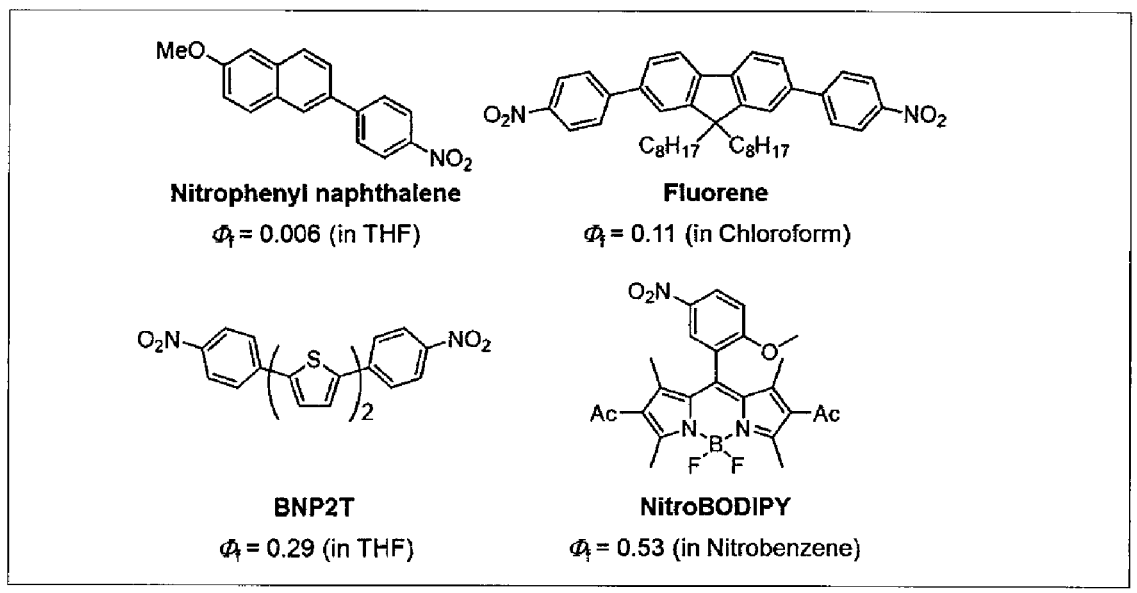
[Fig. 4]
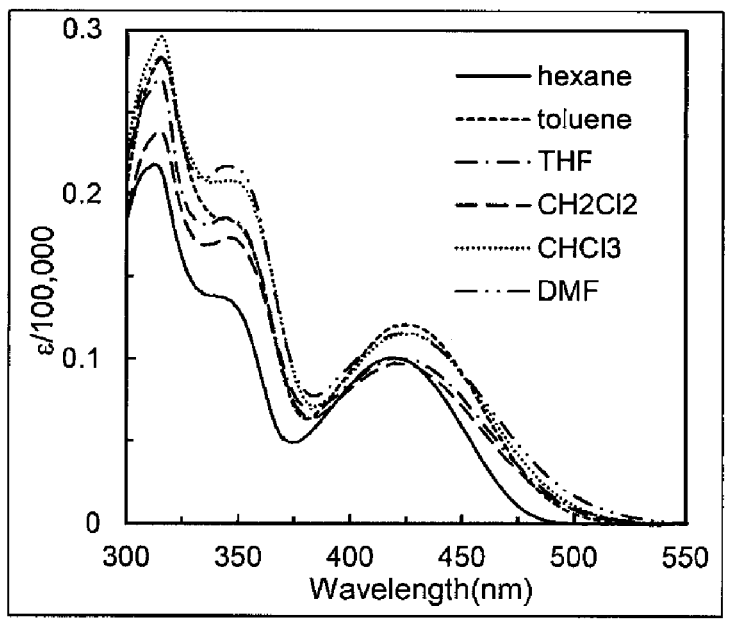

[Fig. 5]
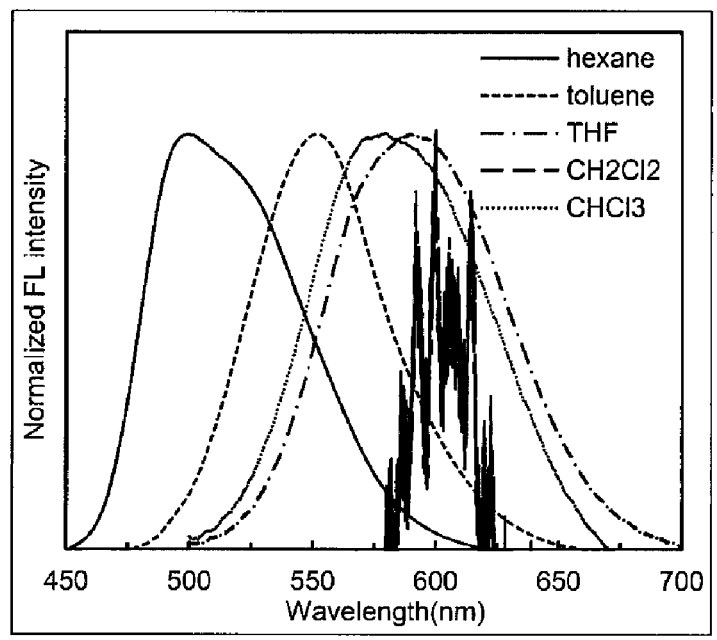
[Fig. 6]
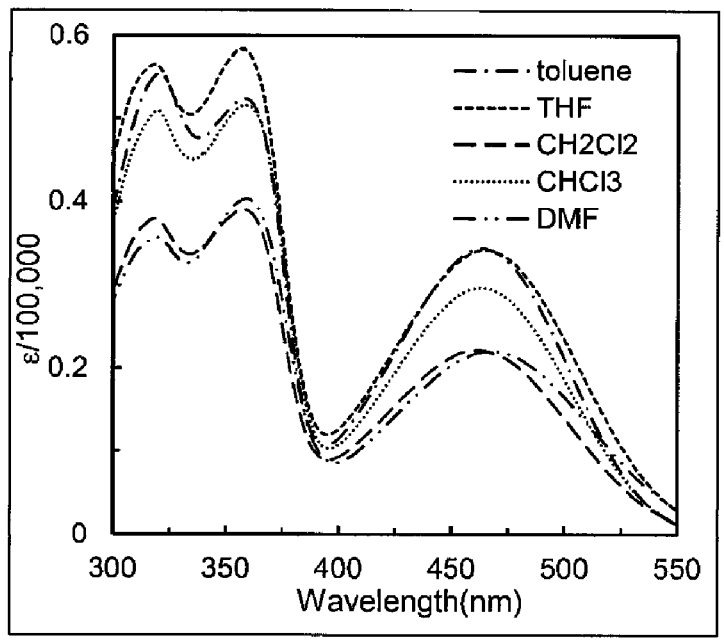

[Fig. 7]
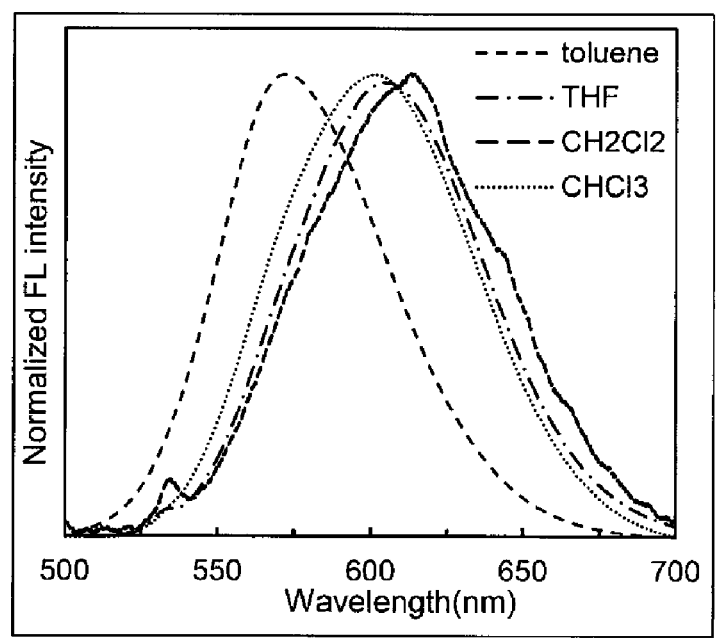

[Fig. 8]
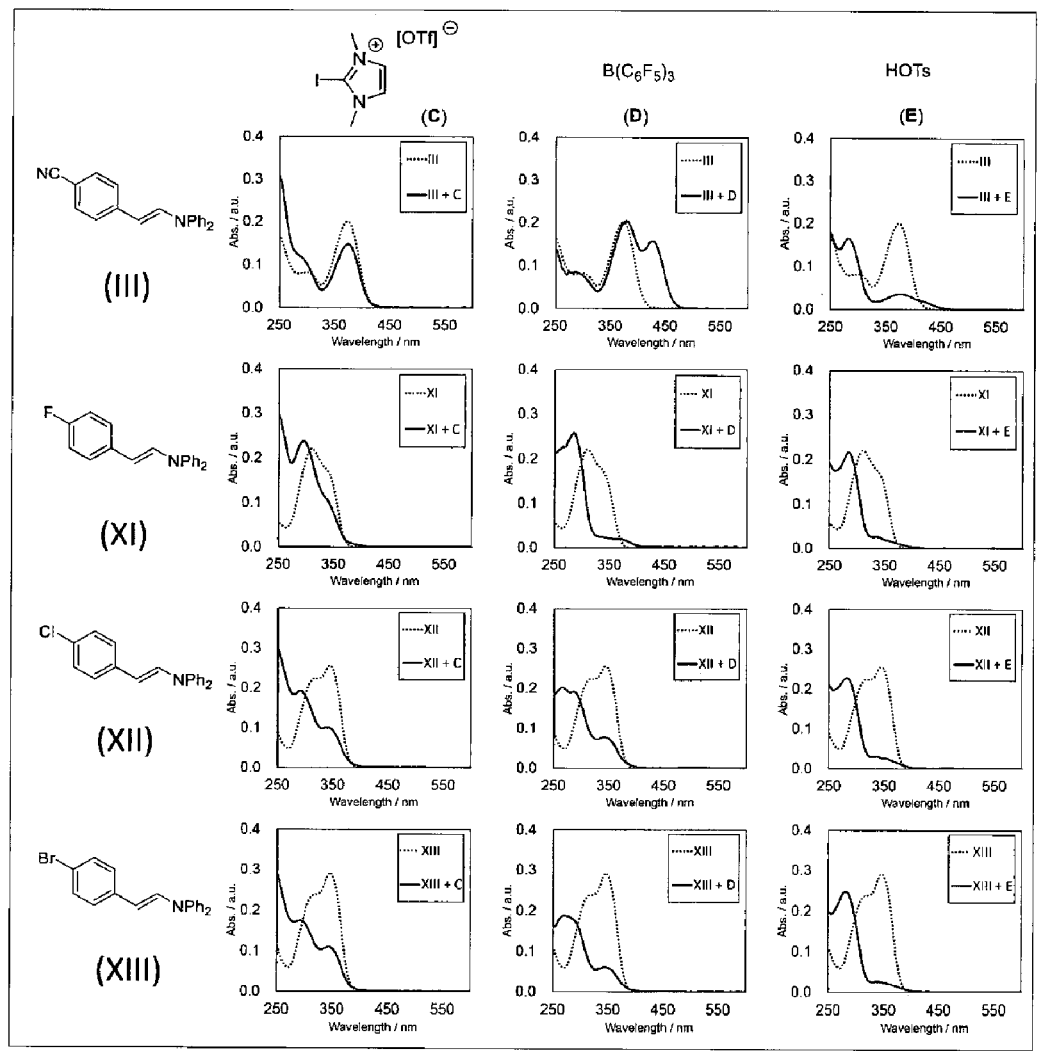

ENAMINE COMPOUND AND USE THEREOF

FIELD OF THE INVENTION

The present invention relates to an enamine compound having an electron-withdrawing group, and to a fluorescent luminescent agent and a photosensitizer containing the enamine compound.

BACKGROUND OF THE INVENTION

A compound in which a donor which is an electron donating group and an acceptor which is an electron-withdrawing group are bonded through a n-conjugated structure in a molecule is expected to be used as a dye for photosensitized solar cells because of its having a strong absorption band in a visible region, and expected to be used as a fluorescent dye or the like because it can generate fluorescence. Such a compound has widely been reported (Patent Documents 1 to 3).

On the other hand, among compounds having an enamine structure, compounds expected to be used as electrophotographic photoreceptors or organic electroluminescent element materials are known (Patent Documents 4 and 5).

CITATION LIST

Patent Document

Patent Document 1: JP-A-2012-144447
Patent Document 2: JP-A-2013-193957
Patent Document 3: JP-A-2010-65069
Patent Document 4: JP-A-2006-269834
Patent Document 5: JP-A-2014-2413

SUMMARY OF THE INVENTION

Problems to be Solved by the Invention

However, in various applications, conventional donor-acceptor type compounds have a complicated chemical structure and take a long manufacturing process, and have not yet been put into practical use.

On the other hand, conventionally known enamine compounds are synthesized from aldehydes and amines, so that their chemical structures are limited, and compounds having various chemical structures have not been reported.

It is an object of the present invention to provide a donor-acceptor type compound having a new structure and its use.

Means for Solving the Problems

Therefore, the present inventors have studied various syntheses of new compounds using metal complexes, and when a hydrosilane compound was reacted with an amide compound in the presence of an iridium complex, the present inventors surprisingly found that an electron-withdrawing group does not react, only an amide bond is selectively reduced, and a new compound having an enamine structure as a donor portion and an electron-withdrawing group as an acceptor portion is easily obtained. Additionally, the obtained enamine compound was found to have a characteristic of absorbing ultraviolet light to visible light and emitting intense fluorescence with high efficiency and to be useful as a fluorescent luminescent agent or a photosensitizer, thereby completing the present invention.

That is, the present invention provides the following [1] to [29].

[1] An enamine compound represented by general formula (1)

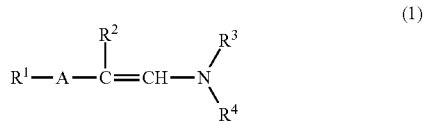

(in the formula:
$R^1$ represents an electron-withdrawing group;
A represents a divalent aromatic hydrocarbon group which may contain a substituent, a divalent aromatic heterocyclic group which may contain a substituent or a divalent unsaturated aliphatic hydrocarbon group which may contain a substituent;
$R^2$ represents a hydrogen atom or a hydrocarbon group which may contain a substituent;
$R^3$ and $R^4$ are the same or different from each other and represent an aromatic hydrocarbon group which may contain a substituent or an aromatic heterocyclic group which may contain a substituent, or $R^3$ and $R^4$ together form a bicyclic aromatic heterocyclic group which may contain a substituent and contains two or more nitrogen atoms or a nitrogen atom and an oxygen atom or a sulfur atom, or a tricyclic aromatic heterocyclic group which may contain a substituent; and
$R^2$ and A, or $R^2$ and $R^3$ may together form a cyclic structure).

[2] An enamine compound described in [1], wherein $R^1$ represents a group selected from a halogen atom, a nitro group, an acyl group, a formyl group, a cyano group, a hydrocarbon oxycarbonyl group, a carboxamide group which may contain a substituent, a perfluoroalkyl group, a dicyanoethenyl group, a Lewis acid residue, an aromatic heterocyclic group, and a group represented by -$A^1$-C($R^5$)=CH—N($R^6$)($R^7$) (where $A^1$ represents a single bond, a divalent aromatic hydrocarbon group which may contain a substituent, a divalent aromatic heterocyclic group which may contain a substituent or a divalent unsaturated aliphatic hydrocarbon group which may contain a substituent, $R^5$ represents a hydrogen atom or a hydrocarbon group which may contain a substituent, $R^6$ and $R^7$ are the same or different from each other and represent an aromatic hydrocarbon group which may contain a substituent or an aromatic heterocyclic group which may contain a substituent, or $R^6$ and $R^7$ together form a bicyclic aromatic heterocyclic group which may contain a substituent and contains two or more nitrogen atoms or a nitrogen atom and an oxygen atom or a sulfur atom, or a tricyclic aromatic heterocyclic group which may contain a substituent, and $R^5$ and $A^1$, or $R^5$ and $R^6$ may together form a cyclic structure).

[3] An enamine compound described in [1] or [2], wherein $R^2$ represents a hydrogen atom, an aliphatic hydrocarbon group which may contain a substituent, or an aromatic hydrocarbon group which may contain a substituent.

[4] An enamine compound described in any of [1] to [3], wherein $R^2$ represents a hydrogen atom, an alkyl group having 1 to 6 carbon atoms, or an aromatic hydrocarbon group having 6 to 10 carbon atoms.

[5] An enamine compound described in any of [1] to [4], wherein $R^1$ represents a group selected from a halogen atom, a nitro group, an acyl group, a cyano group, a hydrocarbon oxycarbonyl group, a carboxamide group which may contain an alkyl group as a substituent, a dicyanoethenyl group, an aromatic heterocyclic group having at least 1 to 4 heteroatoms, and a group represented by -A¹-C(R⁵)=CH—N(R⁶)(R⁷) (where A¹ represents an optionally substituted aromatic heterocyclic group having 1 to 4 heteroatoms, and A¹, R⁵, R⁶ and R⁷ represent the same meanings as claim 2).

[6] An enamine compound described in any of [1] to [5], wherein A represents an optionally substituted divalent aromatic hydrocarbon group having 6 to 18 carbon atoms, a divalent aromatic heterocyclic group which may contain a substituent, an alkenylene group which may contain a substituent, or an alkynylene group which may contain a substituent.

[7] An enamine compound described in any of [1] to [6], wherein R² and A, or R² and R³ together form an aromatic hydrocarbon group which may contain a substituent or an aromatic heterocyclic group which may contain a substituent.

[8] An enamine compound described in [7], wherein at least one of the substituents is an electron-withdrawing group selected from a halogen atom, a nitro group, an acyl group, a formyl group, a hydrocarbon oxycarbonyl group, a carboxamide group which may contain an alkyl group as a substituent, a perfluoroalkyl group, a dicyanoethenyl group, and an optionally substituted aromatic heterocyclic group having 1 to 4 heteroatoms.

[9] An enamine compound described in any of [1] to [8], wherein the tricyclic aromatic heterocyclic group formed by R³ and R⁴ or R⁶ and R⁷ together is a carbazolyl group, a phenoxazinyl group, a phenothiazinyl group, or a dihydrophenazinyl group, the heterocyclic group may be substituted with a $C_{1-6}$ alkyl group, a $C_{1-6}$ alkoxy group, a halogen atom, a sulfide group, an amino group, a boryl group, a silyl group, an acyl group, a formyl group, an alkoxycarbonyl group or a carboxamide group.

[10] An enamine compound described in any of [1] to [9], wherein the cyclic structure formed by R² and A or R⁵ and A¹ together is an indenyl group, a benzofuranyl group, a benzothienyl group, an indolyl group, a benzoborolyl group or a benzosilolyl group (these groups may be substituted with a $C_{1-6}$ alkyl group, a $C_{1-6}$ alkoxy group or a halogen atom).

[11] An enamine compound described in any of [1] to [10], wherein the cyclic structure formed by R² and R³ or R⁵ and R⁶ together is a structure represented by the following groups:

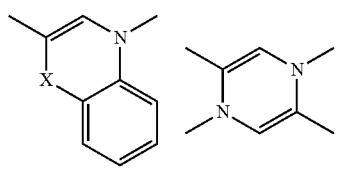

(where X represents O, S, NR¹¹, BR¹², C(R¹²)₂ or Si(R¹²)₂, R¹¹ represents a hydrogen atom or an alkyl group, and R¹² represents an alkyl group), these cyclic structures may be substituted with a $C_{1-6}$ alkyl group, a $C_{1-6}$ alkoxy group, a halogen atom, an acyl group, a formyl group, a cyano group, an alkoxycarbonyl group, a carboxamide group, a perfluoroalkyl group, a dicyanoethenyl group or an aromatic heterocyclic group.

[12] A method for producing an enamine compound represented by general formula (1)

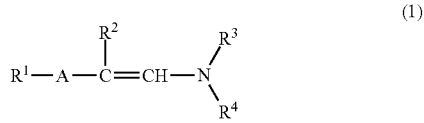

(in the formula:

R¹ represents an electron-withdrawing group;

A represents a divalent aromatic hydrocarbon group which may contain a substituent, a divalent aromatic heterocyclic group which may contain a substituent or a divalent unsaturated aliphatic hydrocarbon group which may contain a substituent;

R² represents a hydrogen atom or a hydrocarbon group which may contain a substituent;

R³ and R⁴ are the same or different from each other and represent an aromatic hydrocarbon group which may contain a substituent or an aromatic heterocyclic group which may contain a substituent, or R³ and R⁴ together form an optionally substituted bicyclic aromatic heterocyclic group containing two or more nitrogen atoms or a nitrogen atom and an oxygen atom or a sulfur atom, or a tricyclic aromatic heterocyclic group which may contain a substituent; and R² and A, or R² and R³ may together form a cyclic structure), comprising:

reacting an amide compound represented by general formula (a)

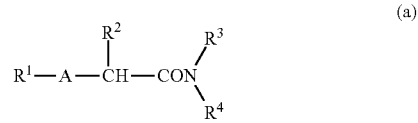

(where R¹, R², R³, R⁴ and A represent the same meanings as above) with a hydrosilane compound in the presence of an iridium complex.

[13] A method for producing an enamine compound, described in [12], wherein the iridium complex is represented by the following general formula (3)

(in the formula, X² represents a halogen atom, and Y and Z each represent a phenyl group, a phenoxy group, a pyrrolyl group, a perfluorophenoxy group or a perfluoroalkoxy group).

[14] A fluorescent luminescent agent composition comprising an enamine compound characterized by having an enamine structure as an electron-donating group and an electron-withdrawing group disposed at a position conjugated to the enamine.

[15] A fluorescent luminescent agent composition comprising an enamine compound represented by the following general formula (1)

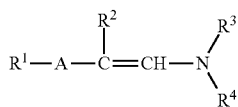

(in the formula:

R[1] represents an electron-withdrawing group;

A represents a divalent aromatic hydrocarbon group which may contain a substituent, a divalent aromatic heterocyclic group which may contain a substituent or a divalent unsaturated aliphatic hydrocarbon group which may contain a substituent;

R[2] represents a hydrogen atom or a hydrocarbon group which may contain a substituent;

R[3] and R[4] are the same or different from each other and represent an aromatic hydrocarbon group which may contain a substituent or an aromatic heterocyclic group which may contain a substituent, or R[3] and R[4] together form an optionally substituted bicyclic aromatic heterocyclic group containing two or more nitrogen atoms or a nitrogen atom and an oxygen atom or a sulfur atom, or a tricyclic aromatic heterocyclic group which may contain a substituent; and R[2] and A, or R[2] and R[3] may together form a cyclic structure).

[16] A fluorescent luminescent agent composition described in [14] or [15], further comprising an electron acceptor.

[17] A fluorescent luminescent agent composition described in [16], wherein the electron acceptor is a cation donor.

[18] A fluorescent luminescent agent composition described in [17], wherein the cation donor is a proton or a halogen cation.

[19] A fluorescent luminescent agent composition described in [18], wherein the proton is a Bronsted acid.

[20] A fluorescent luminescent agent composition described in [18], wherein the halogen cation is a halogen bond donor.

[21] A fluorescent luminescent agent composition described in [16], wherein the electron acceptor is a Lewis acid.

[22] A photosensitizer composition comprising an enamine compound characterized by having an enamine structure as an electron-donating group and an electron-withdrawing group disposed at a position conjugated to the enamine.

[23] A photosensitizer composition comprising an enamine compound represented by the following general formula (1)

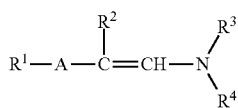

(in the formula:

R[1] represents an electron-withdrawing group;

A represents a divalent aromatic hydrocarbon group which may contain a substituent, a divalent aromatic heterocyclic group which may contain a substituent or a divalent unsaturated aliphatic hydrocarbon group which may contain a substituent;

R[2] represents a hydrogen atom or a hydrocarbon group which may contain a substituent;

R[3] and R[4] are the same or different from each other and represent an aromatic hydrocarbon group which may contain a substituent or an aromatic heterocyclic group which may contain a substituent, or R[3] and R[4] together form an optionally substituted bicyclic aromatic heterocyclic group containing two or more nitrogen atoms or a nitrogen atom and an oxygen atom or a sulfur atom, or a tricyclic aromatic heterocyclic group which may contain a substituent; and R[2] and A, or R[2] and R[3] may together form a cyclic structure).

[24] A photosensitizer composition described in [22] or [23], further comprising an electron acceptor.

[25] A photosensitizer composition described in [24], wherein the electron acceptor is a cation donor.

[26] A photosensitizer composition described in [25], wherein the cation donor is a proton or a halogen cation.

[27] A photosensitizer composition described in [26], wherein the proton is a Bronsted acid.

[28] A photosensitizer composition described in [26], wherein the halogen cation is a halogen bond donor.

[29] A photosensitizer composition described in [24], wherein the electron acceptor is a Lewis acid.

Effects of the Invention

According to the method of the present invention, the electron-withdrawing group does not react and only the amide bond is selectively reduced, so that compounds having various electron-withdrawing groups can be easily produced using an amide compound as a raw material. The enamine compound of the present invention exhibits excellent fluorescence emission even when the enamine compound has a nitro group which behaves as a quenching group, emits fluorescence even under fat-soluble conditions such as hexane, emits red light, and has a high quantum yield, and is therefore useful as a fluorescent luminescent agent and a photosensitizer. Considering such a photosensitization effect, the enamine compound of the present invention can be applied not only to a fluorescent probe, but also to an organic solar cell, an organic transistor, an organic EL, a nonlinear optical material (function of converting a wavelength of light, amplifying light, changing a refractive index according to a light intensity), and the like.

BRIEF DESCRIPTION OF THE DRAWINGS

FIG. 1 shows the ultraviolet-visible absorption spectrum ($1.0 \times 10^{-5}$ M in hexane, toluene, THF, chloroform, dichloromethane, DMF solvents) of compound (III).

FIG. 2 shows the fluorescence spectrum ($1.0 \times 10^{-5}$ M in hexane, toluene, THF, chloroform, dichloromethane, DMF solvents) of compound (III).

FIG. 3 shows the quantum yield of light emission of a compound similar to the compound of the present invention.

FIG. 4 shows the UV-visible absorption spectrum ($1.0 \times 10^{-5}$ M in hexane, toluene, THF, chloroform, dichloromethane, DMF solvents) of compound (IV).

FIG. 5 shows the fluorescence spectrum ($1.0 \times 10^{-5}$ M in hexane, toluene, THF, chloroform, dichloromethane, DMF solvents) of compound (IV).

FIG. 6 shows the ultraviolet-visible absorption spectrum ($1.0 \times 10^{-5}$ M in hexane, toluene, THF, chloroform, dichloromethane, and DMF solvents) of compound (VIII).

FIG. 7 shows the fluorescence spectrum ($1.0 \times 10^{-5}$ M in hexane, toluene, THF, chloroform, dichloromethane, DMF solvents) of compound (VIII).

FIG. 8 shows the ultraviolet-visible absorption spectra ($1.0 \times 10^{-4}$ M in methylene chloride solvent) of compounds (III), (XI), (XII) and (XIII) to which reagents C, D, and E each are added (Solid line: additive present, Dotted line: no additive.).

DETAILED DESCRIPTION OF THE INVENTION

The enamine compound of the present invention is characterized by having an enamine structure as an electron-donating group and an electron-withdrawing group disposed at a position conjugated to the enamine. The enamine compound of the present invention has one or more enamine structures therein. Between the electron-donating group (enamine) and the electron-withdrawing group, there exists a conjugated structure in which the electron-donating group and the electron-withdrawing group are conjugated. The electron energy level for fluorescence emission can be adjusted by the length of the conjugated structure and the type and number of substituents of the conjugated structure. It is preferable that the conjugated structure is adjacent to each enamine structure from the viewpoint of adjusting the fluorescence wavelength and the fluorescence intensity, and it is more preferable that at least one conjugated structure is divalent.

Specific examples of the enamine compound of the present invention are represented by general formula (1), and characterized by having an electron-withdrawing group on $R^1$.

As the electron-withdrawing group represented by $R^1$, there may be mentioned a group selected from a halogen atom, a nitro group, an acyl group, a formyl group, a cyano group, a hydrocarbon oxycarbonyl group, a carboxamide group which may contain a substituent, a perfluoroalkyl group, a dicyanoethenyl group, a Lewis acid residue, an aromatic heterocyclic group, and a group represented by $-A^1-C(R^5)=CH-N(R^6)(R^7)$ (wherein $A^1$, $R^5$, $R^6$ and $R^7$ have the same meanings as described above).

Examples of the halogen atom include a fluorine atom, a chlorine atom, a bromine atom and an iodine atom.

Examples of the acyl group include an alkanoyl group. Specific examples thereof include $C_{1-6}$ alkanoyl groups.

Examples of the hydrocarbon oxycarbonyl group include an aralkyloxycarbonyl group, an alkoxycarbonyl group, an aryloxycarbonyl group, and the like. Specifically, there can be cited phenyl $C_{1-6}$ alkyloxycarbonyl groups, $C_{1-6}$ alkoxycarbonyl groups, and $C_{6-12}$ aryloxycarbonyl groups.

The carboxamide group which may contain a substituent includes a carboxamide group which may have an alkyl group, and specifically includes a carboxamide group, an N-alkylcarboxamide group, and an N,N-dialkylcarboxamide group.

The dicyanoethenyl group includes a $(CN)_2C=CH-$ group.

The Lewis acid residue includes a pinacolboryl group, a catecholboryl group, and a diarylboryl group.

The aromatic heterocyclic group includes an aromatic heterocyclic group of a single ring or a fused ring having a nitrogen atom, an oxygen atom, or a sulfur atom as a heteroatom. Specifically, there may be mentioned a group derived from pyridine, pyridazine, pyrimidine, pyrazine, benzothiazole, benzothiadiazole, benzoxadiazole, benzotriazole, benzotriazine, quinoxaline, cinnoline, prazine, qui-nazoline, quinoline, isoquinoline, thiazolothiazole, oxazoloxazole, imidazole, pyrazole, triazole, tetrazole, oxazole, thiazole, a fluorene group, a dibenzofuran group, a adibenzothiophene group, a carbazole group, or the like. Among these, a nitrogen-containing aromatic heterocyclic group is preferable, an aromatic heterocyclic group having two or more $-C=N-$bonds is more preferable, and a group derived from benzothiadiazole, benzoxadiazole, benzotriazole, quinoxaline, thiazolothiazole or oxazoloxazole is particularly preferable.

An enamine compound in which $R^1$ is a group represented by $-A^1-C(R^5)=CH-N(R^6)(R^7)$ has the following structure:

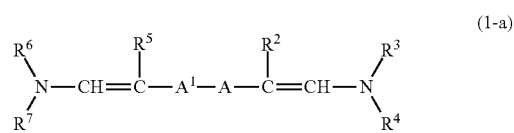

(1-a)

(where A, $A^1$, $R^2$, $R^3$, $R^4$, $R^5$, $R^6$ and $R^7$ are the same as above).

This compound (1-a) is an example of a compound having two donors with enamine structures and acceptors in A and $A^1$.

A and $A^1$ each represent a single bond, a divalent aromatic hydrocarbon group which may contain a substituent, a divalent aromatic heterocyclic group which may contain a substituent or a divalent unsaturated aliphatic hydrocarbon group which may contain a substituent. However, both A and $A^1$ are not single bonds at the same time. Among these, a divalent aromatic hydrocarbon group having 6 to 18 carbon atoms, an aromatic heterocyclic group having an oxygen atom or a sulfur atom, an alkenylene group, or an alkynylene group is preferable (these may contain one or more substituents).

The number of substituents of the aromatic hydrocarbon group, the aromatic heterocyclic group or the unsaturated aliphatic hydrocarbon group of A and $A^1$ is 1 or 2 or more, preferably from 1 to 4, more preferably from 1 to 3. When these substituents are two or more, they may be the same or different.

In general formula (1), when $R^1$ is a group other than $A^1-C(R^6)=CH-N(R^6)(R^7)$, the substituent on A may be either an electron-withdrawing group or an electron-donating group. Examples of the electron-donating group include an alkyl group, an alkoxy group, and the like.

In general formula (1), when $R^1$ is $-A^1-C(R^6)=CH-N(R^6)(R^7)$, at least one of the substituents on A and $A^1$ is preferably an electron-withdrawing group. Such an electron-withdrawing group is more preferably an electron-withdrawing group selected from a halogen atom, a nitro group, an acyl group, a formyl group, a cyano group, a hydrocarbon oxycarbonyl group, a carboxamide group which may contain an alkyl group as a substituent, a perfluoroalkyl group, a dicyanoethenyl group, and an aromatic heterocyclic group having 1 to 4 heteroatoms.

Examples of the divalent aromatic hydrocarbon group include a phenylene group, a naphthalene group, a biphenylene group, a triphenylene group, an indenylene group, a fluorene group, an anthracenylene group, a phenanthrenylene group, a naphthacene group, a pyrenylene group, a chrysenylene group, and a coronenylene group.

Examples of the divalent aromatic heterocyclic group include a thienylene group, a furanylene group, a borolane group (boracyclopentadienylene group), a sirolane group (silacyclopentadienylene group), and the like. Examples of the alkenylene group and the alkynylene group include a vinylene group, a di(vinylene) group, an acetylene group, a di(acetylene) group, and the like. These groups may contain one or more electron-withdrawing groups as substituents.

$R^2$ and $R^5$ each represent a hydrogen atom or a hydrocarbon group which may contain a substituent. Examples of the hydrocarbon group include an alkyl group having 1 to 4 carbon atoms and an aromatic hydrocarbon group having 6 to 18 carbon atoms. Specific examples include a methyl group, an ethyl group, an n-propyl group, isopropyl group, and a phenyl group. Examples of a group that these hydrocarbon groups may contain as a substituent include a halogen atom, a $C_{1-4}$ alkyl group, a $C_{1-4}$ alkoxy group, a sulfide group, an amino group, a boryl group, a silyl group, an acyl group, a formyl group, an alkoxycarbonyl group, a carboxamide group, and the like.

$R^3$, $R^4$, $R^6$ and $R^7$ are the same or different from each other and represent an aromatic hydrocarbon group which may contain a substituent or an aromatic heterocyclic group which may contain a substituent, or $R^3$, $R^4$, $R^6$ and $R^7$ together form a bicyclic aromatic heterocyclic group which may contain a substituent and contains two or more nitrogen atoms or a nitrogen atom and an oxygen atom or a sulfur atom, or a tricyclic aromatic heterocyclic group which may contain a substituent. Among these, an aromatic hydrocarbon group which may contain a substituent and has 6 to 18 carbon atoms or an aromatic heterocyclic group which may contain a substituent and has 1 to 4 nitrogen atoms, oxygen atoms or sulfur atoms is preferable.

As the aromatic hydrocarbon group, a phenyl group, a naphthyl group, a biphenyl group, a triphenyl group, and an anthracenyl group are preferred. The aromatic heterocyclic group includes a thienyl group, a furyl group, a pyrrolyl group, a pyridyl group, a benzofuranyl group, a quinolyl group and so on. As a group that the aromatic hydrocarbon group or the aromatic heterocyclic group may contain as a substituent, there may be mentioned a $C_{1-6}$ alkyl group, a $C_{1-6}$ alkoxy group, a halogen atom, a nitro group, a sulfide group, an amino group, a boryl group, a silyl group, an acyl group, a formyl group, an alkoxycarbonyl group, a carboxamide group, and the like.

Examples of the aromatic hydrocarbon group which may contain a substituent or the aromatic heterocyclic group which may contain a substituent, represented by $R^3$ or $R^4$, include a group represented by —$R^3$—N($R^{10}$)—CH=C($R^9$)-$A^2$-$R^8$ (where $R^3$ represents a hydrocarbon group or an aromatic heterocyclic group, $R^8$ represents the same group as the $R^1$, $A^2$ represents the same meaning as the A, $R^9$ represents the same meaning as the $R^2$, and $R^{10}$ represents the same meaning as the $R^7$). Specific examples of $R^8$, $R^9$, $R^{10}$ and $A^2$ include the same as those of $R^2$, R. $R^4$ and A. Examples of an enamine compound in which $R^3$ or $R^4$ represents a group represented by the above-mentioned formula include the following compounds:

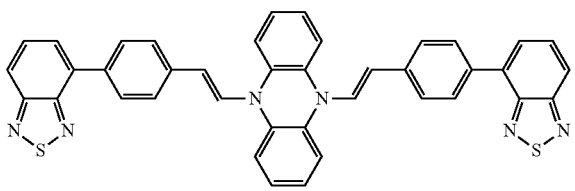

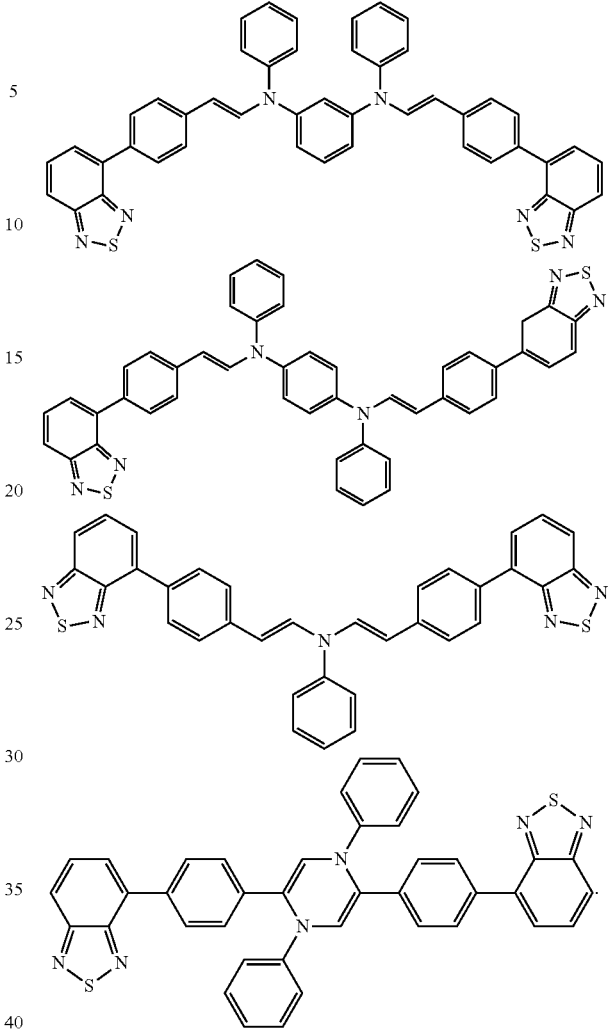

The bicyclic aromatic heterocyclic group having two or more nitrogen atoms or a nitrogen atom and an oxygen or sulfur atom, that $R^3$ and $R^4$ or $R^6$ and $R^7$ together form, includes a purinyl group, a phthalazinyl group, a naphthyridinyl group, a quinoxalinyl group, a quinazolinyl group, a benzoxazinyl group, a benzothiazinyl group, and the like.

The tricyclic aromatic heterocyclic group formed by $R^3$ and $R^4$ or $R^6$ and $R^7$ together is a tricyclic aromatic heterocyclic group containing the nitrogen atom adjacent to $R^3$ and $R^4$ or $R^6$ and $R^7$, and includes a carbazolyl group, a phenoxazinyl group, a phenothiazinyl group, a dihydrophenazinyl group, and the like. Examples of a group which the heterocyclic group may contain as a substituent include a $C_{1-6}$ alkyl group, a $C_{1-6}$ alkoxy group, a halogen atom, a nitro group, a sulfide group, an amino group, a boryl group, a silyl group, an acyl group, a formyl group, an alkoxycarbonyl group, and a carboxamide group.

The cyclic structure which is formed by $R^2$ and A or $R^5$ and $A^1$ together include an aromatic hydrocarbon group which may contain a substituent or an aromatic heterocyclic group which may contain a substituent. Examples of these rings include an indenyl group, a benzofuranyl group, a benzothienyl group, an indolyl group, a benzoborolyl group, and a benzosilolyl group. Examples of a group that these groups may contain as a substituent include a $C_{1-6}$ alkyl group, a $C_{1-6}$ alkoxy group, a halogen atom, and the like.

The cyclic structure which is formed by $R^2$ and $R^3$ or $R^5$ and $R^6$ together include a heterocyclic group which may contain a substituent. Examples of this ring include the following groups:

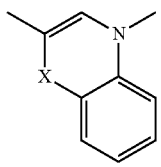 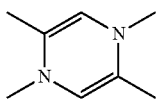

(where X represents O, S, $NR^{11}$, $BR^{12}$, $C(R^{11})_2$, or $Si(R^{12})_2$, $R^{11}$ represents a hydrogen atom or an alkyl group, and $R^{12}$ represents an alkyl group).

Examples of a group that these cyclic structure may contain as a substituent include an electron-withdrawing group such as a halogen atom, a nitro group, an acyl group, a formyl group, a cyano group, an alkoxycarbonyl group, a carboxamide group, a perfluoroalkyl group, a dicyanoethenyl group and an aromatic heterocyclic group, in addition to a $C_{1-6}$ alkyl group and a $C_{1-6}$ alkoxy group.

Specific examples of compounds in which $R^2$ and A, $R^2$ and $R^3$, $R^3$ and $R^4$ together form a ring are shown below.

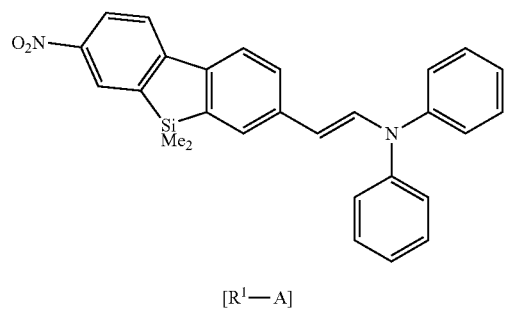

[$R^1$—A]

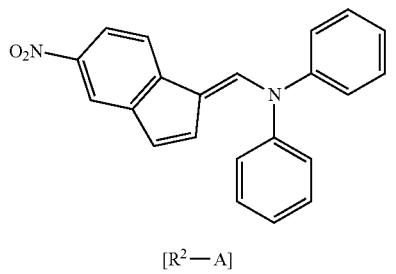

[$R^2$—A]

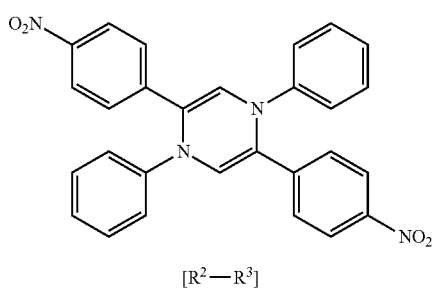

[$R^2$—$R^3$]

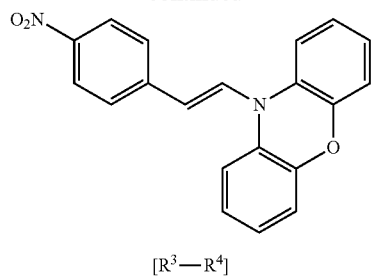

[$R^3$—$R^4$]

Additionally, enamine compounds of the present invention also include geometric isomers, cis-trans isomers, and optical isomers.

Enamine compound (1) of the present invention can be obtained by reacting an amide compound represented by general formula (a)

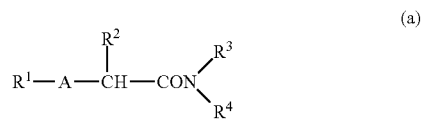

(in which $R^1$, A, $R^2$, $R^3$ and $R^4$ are the same as above) with a hydrosilane compound in the presence of an iridium complex, for example.

Amide compound (a) serving as a raw material is produced, for example, according to the following formula:

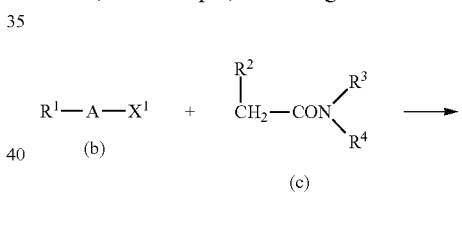

(wherein $X^1$ represents a leaving group, preferably a halogen atom, and A, $R^1$, $R^2$, $R^3$ and $R^4$ are the same as described above).

That is, the amide compound of formula (a) can be produced by cross-coupling a compound of formula (b) and a compound of formula (c) in use of a palladium catalyst.

In the cross-coupling reaction, for example, the amide compound of formula (c) is reacted with a base such as butyllithium, and then reacted with zinc chloride, aluminum chloride, or the like, followed by being reacted with a halide of formula (b) in the presence of a palladium catalyst.

The hydrosilane compound reacted with the amide compound of formula (a) is not particularly limited as long as it is a compound having a hydrosilane (SiH) group, and for example, tetramethyldisiloxane ($Me_2HSiOSiHMe_2$), octamethyltetrasiloxane ($Me_3SiOSiHMeOSiHMeOSiMe_3$), polymethylhydrosiloxane $(MeHSiO)_n$, or the like is used.

As the iridium complex, a complex represented by the following general formula (3):

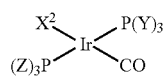

(wherein $X^2$ represents a halogen atom and Y and Z each represent a phenyl group, a phenoxy group, a pyrrolyl group, a perfluorophenoxy group or a perfluoroalkoxy group) may be cited.

The reaction between the amide compound of formula (a) and the hydrosilane compound may be carried out in the presence of a small amount of the iridium complex, in a solvent such as toluene, benzene, xylene, THF, methylene chloride or the like, under an inert gas atmosphere at from 15 to 50° C. for from 30 minutes to 10 hours.

Enamine compound (1) of the present invention is a donor-acceptor type compound having an enamine structure as a donor moiety and an electron-withdrawing group as an acceptor moiety, and absorbs ultraviolet light to visible light to generate fluorescence emission. Its fluorescence emission properties result in strong fluorescence even for compounds with a stable nitro group, which are referred to as a quenching group. Fluorescence emission of the enamine compound of the present invention occurs also in a fat-soluble medium such as hexane, and exhibits a fluorescence solvatochromism phenomenon in which the color tone of the fluorescence is changed according to a change in the polarity of the solvent. Furthermore, the quantum yield of fluorescence emission of enamine compound (1) of the present invention is extremely high, and red light emission on the longer wavelength side is also possible. Therefore, enamine compound (1) of the present invention is useful as a fluorescent luminescent agent and a photosensitizer in various fields. The application fields therefor include an organic solar cell, an organic transistor, an organic EL, a fluorescent probe of biomolecule, a nonlinear optical material (function of converting a wavelength of light, amplifying light, changing a refractive index according to a light intensity), a multiphoton absorbing material and the like. Especially, the fluorescent probe of the biomolecule is useful as a biological membrane probe, a probe for detecting an antigen-antibody reaction, a probe for detecting a site-specific nucleotide sequence, or the like.

When enamine compound (1) of the present invention is used as a fluorescent luminescent agent or a photosensitizer, only enamine compound (1) may be used, but it can be used in a form suitable for these uses, for example, in a form of a composition containing enamine compound (1). The composition may contain, in addition to enamine compound (1), an electron acceptor, a solvent, or any other substance necessary for the application.

The electron acceptor has an empty orbital capable of accepting an electron pair, and interacts with enamine compound (1) to receive an electron pair from the enamine compound to form a complex. As the electron acceptor, there may be cited cationic species in addition to Lewis acids. Cationic species are represented by protons and halogen cations. Usually, protons are provided by Bronsted acids while halogen cations are provided by halogen bond donors. Additionally, tetracyanoethylene and quinones, which can form a charge transfer complex when reacted with an electron donor such as enamine, may also be cited as the electron acceptor.

Halogen cations have empty orbitals that can accept electron pairs, and therefore it may interact with the enamine compound to accept electron pairs and form a complex. Furthermore, a compound I—Cl in which halogens are bound to each other is polarized to $I(\delta+)-Cl(\delta-)$ because of the large difference in electronegativity, thereby forming an empty orbital on iodine that can accept an electron pair, thus forming a complex with an enamine compound. In addition, $I-C_6F_5$ has a low electron density on the benzene ring because of the high electronegativity of F, in which an unshared electron pair present on iodine moves to compensate for the electron density on the benzene ring. Thus a resonance structure where iodine is positively strongly polarized is formed and stabilized. This structure also has an empty orbital that can accept the electron pair and therefore it may form a complex with the enamine compound. Furthermore, an iodoimidazolinium salt is stable because it forms a salt of a $PF_6$ anion and an imidazole cation, in which electron moves to compensate for the electron density on the imidazole ring to form a resonance structure where iodine is positively strongly polarized, thereby getting stabilized. An empty orbital is formed on the iodine to accept an electron pair, and therefore a complex is formed with the unpaired electron of the enamine compound.

1) halogen cation

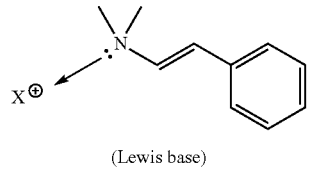

(Lewis base)

2) I—Cl

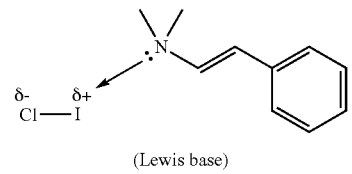

(Lewis base)

3) $C_6F_5I$

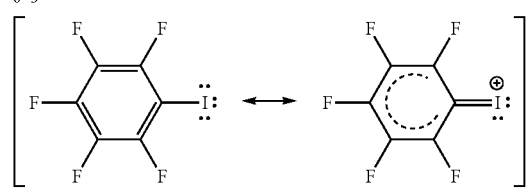

(Lewis base)

4) Iodoimidazolinium salt

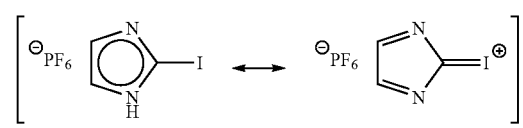

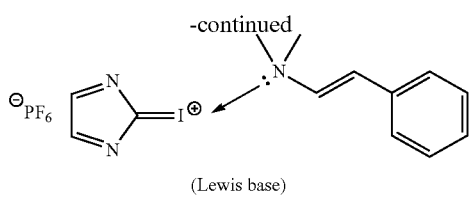

(Lewis base)

Examples of the Bronsted acids include a carboxylic acid such as acetic acid and trifluoroacetic acid, a sulfonic acid such as fluorosulfonic acid, methanesulfonic acid, ethylsulfonic acid, 4-dodecylbenzenesulfonic acid, heptadecafluorooctanesulfonic acid, camphorsulfonic acid, p-toluenesulfonic acid, 2,4-dinitrobenzenesulfonic acid, 1-naphthalenesulfonic acid and mesitylenesulfonic acid, a phosphonic acid such as methylphosphonic acid, ethylphosphonic acid, propylphosphonic acid, tert-butylphosphonic acid, octylphosphonic acid and hexadecylphosphonic acid, a phosphinic acid such as dimethylphosphinic acid, phenylphosphinic acid, diphenylphosphinic acid and diisooctylphosphinic acid. Examples of the Lewis acid include $BF_3$, $BBr_3$, $B(NMe_2)_3$, tris(pyrrolidino)borane, tris(mesityl)borane, triethyl borate, tributyl borate, Alpine borane, triphenylborane, $B(C_6F5)_3$, $AlCl_3$, $FeCl_3$, $FeBr_3$, $ZnCl_2$, $InCl_3$, $TiCl_4$, and metallic triflate salts. The halogen bond donor can accept an unpaired electron of a Lewis base functional group such as enamine and phenylpyridine in an empty orbital generated by the structure of the halogen donor itself. Specific examples include a perfluoroiodiobenzene, a halogen molecule, a halogen cation, a perfluoroiodialkane, a N-halogenodicarboxylic imide, a 1,2,3-triazolinium-5-halide, a N,N-dialkylimidazolinium-2-halide, a 2-halogenoisoindolyl-1,3-dione, a 2-halogenobenzo[d]isothiazol-3(2H)-one 1,1-dioxide, a 2-halogeno-5-nitroisoindolyl-1,3-dione, a 2-halogeno-3,4-dimethylthiazol-3-inium trifluuorosulfonate and the like.

Examples

Referring now to Examples, the present invention is further described in detail; however, the invention is not limited to these Examples.

Synthesis of the iridium complex was carried out using a Schlenk technique or a glove box, wherein all operations were performed under an inert gas atmosphere. All of solvents used for preparation of a transition metal compound were used after deoxygenation and dehydration were carried out by a known method.

A reaction for synthesis of an enamine compound, a reaction between an amide compound and a hydrosilane, and a solvent purification were all carried out under an inert gas atmosphere, and solvents and the like used in the various reactions were all used after deoxygenation and dehydration were carried out in advance by a known method.

$^1H$, $^{13}C$, $^{31}P$, and $^{19}F$-NMR measurements were conducted using JNM-ECA600 and JNM-ECA400 produced by JEOL Ltd., IR measurement was conducted using FT/IR-550 produced by JASCO Corporation, and elemental analysis was performed by using 2400II/CHN manufactured by Perkin Elmer. Absorption spectrum was measured using a V-570 spectrophotometer produced by JASCO Corporation in such a manner as to measure the transmitted light in use of a 1 cm square quartz container. Fluorescence spectra were measured using a F-4500 type fluorescence spectrophotometer manufactured by Hitachi, Ltd. The samples were measured for reflected light using a 1 cm square complete-transparent SQ cell.

In the structural formula shown below, hydrogen atoms are omitted in accordance with a conventional expression method. Me represents a methyl group, and Ph represents a phenyl group.

(1) Synthesis of Iridium Complex

[Example 1] Synthesis of Iridium Complex A

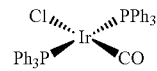

A 50 mL Schlenk reactor tube was charged with a stirrer, $[Ir(COD)Cl]_2$ weighed out in an amount of 100 mg (0.15 mmol) and triphenylphosphine weighed out in an amount of 158 mg (0.60 mmol), and argon-substitution was carried out three times. The reactor was further charged with 5 mL of dehydrated THF in a condition cooled to −78° C. and then stirred while keeping −78° C. for 1 hour. Thereafter, the solution was frozen by using liquid nitrogen, followed by a degassing operation under reduced pressure three times. The reaction container was again returned to −78° C. and the interior of the container was replaced with CO (1 atm). Thereafter, stirring was carried out for 1 hour at −78° C. and at room temperature each. The solvent was distilled off under reduced pressure and the resulting yellow solid was washed with dehydrated hexane (5 mL×3 times). Thereafter, it was dried in vacuum to obtain an iridium complex IrCl(CO) $(PPh_3)_2$ (A) in the form of a yellow solid (171 mg, 73% yield). The resulting compound was identified by 1H-NMR, by $^{31}P$-NMR, and by IR spectrum.

$^1H$-NMR ($CDCl_3$, 400 MHz): δ7.38-7.72 (m, 30H, Ph),
$^{31}P$-NMR ($CDCl_3$, 243 MHz): δ-24.73 (s),
IR (KBr pellet): ν=1953 (CO) $cm^{-1}$

[Example 2] Synthesis of Iridium Complex B

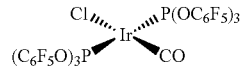

A 50 mL Schlenk reactor tube was charged with a stirrer, $[Ir(COD)Cl]_2$ weighed out in an amount of 100 mg (0.15 mmol) and tris(pentafluorophenyl)phosphite weighed out in an amount of 345 mg (0.60 mmol) in a glove box. The reactor was further charged with 5 mL of dehydrated THF in a condition cooled to −78° C. and then stirred while keeping −78° C. for 1 hour. Thereafter, the solution was frozen by using liquid nitrogen, followed by a degassing operation under reduced pressure three times. The reaction container was again returned to −78° C. and the interior of the container was replaced with CO (1 atm). Thereafter, stirring was carried out for 1 hour at −78° C., and then the solvent was distilled off under reduced pressure while keeping −78° C. The resulting yellow solid was filtered by 1 mL of dehydrated THF. The filtrate was concentrated and then dissolved in 20 mL of dehydrated pentane and allowed to stand at −30° C. for 24 hours to obtain iridium complex IrCl(CO){$P(OC_6F_5)_3$}$_2$ (B) as yellow needle-like crystals (178 mg, 84% yield). The resulting compound was identified by $^{13}C$-NMR, $^{19}F$-NMR, $^{31}P$-NMR, IR spectrum and elemental analysis, and its structure was confirmed by single-crystal X-ray structural analysis.

$^{13}C\{^{19}F\}$-NMR (CDCl$_3$, 151 MHz): δ125.0 (ipso-$\underline{C}_6F_5$), 138.1 (C$_6$F$_5$), 140.0 (C$_6$F$_5$), 141.0 (C$_6$F$_5$), 165.1 (CO)

$^{19}$F-NMR (CDCl$_3$, 565 MHz): δ-161.7 (dd, $J_{F-F}$=20.7 Hz, m-C$_6$$\underline{F}_5$), -156.7 (t, $J_{F-F}$=20.7 Hz, p-C$_6$$\underline{F}_5$), -151.8 (d, $J_{F-F}$=20.7 Hz, o-C$_6$$\underline{F}_5$)

$^{31}$P-NMR (CDCl$_3$, 243 MHz): δ108.0 (s)

IR (KBr pellet): ν=2052 (CO) cm$^{-1}$

Anal. Calcd for C$_{37}$O$_7$F$_{30}$P$_2$ClIr: C, 31.39; H, 0.00 Found: C, 31.56; H, 0.12.

(2) Reaction of Hydrosilane with Amide Compound Using Iridium Complex

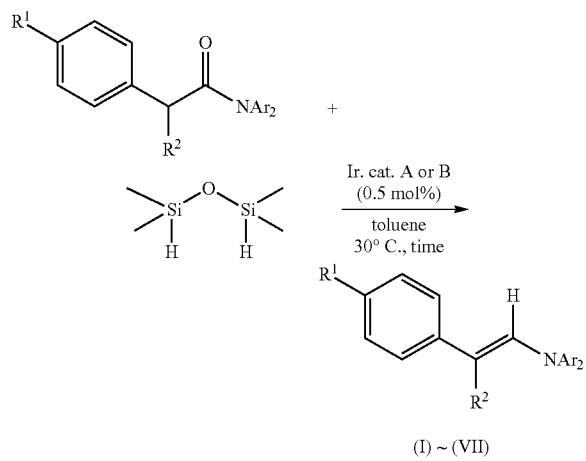

[Example 3] Synthesis of N-(2-(4-acetylphenyl)-vinyl)-N,N-diphenylamine (I; R$^1$=COMe, R$^2$=H, NAr$_2$=NPh$_2$) Using Iridium Complex A A 20 mL eggplant-shaped flask was charged with a stirrer and 4-acetylphenyl-N,N-diphenylacetamide weighed out in an amount of 165 mg (0.5 mmol), and a three-way cock was attached thereto. The reaction container was brought into a glove box, and 0.5 mL of a 1 mL solution of dehydrated toluene in which iridium complex A (2.0 mg, 0.0025 mmol) was dissolved was added thereto. Then the reaction container was further charged with 4 mL of dehydrated toluene and anisole (54 μl, 0.5 mmol) as an internal standard reagent and stirred for 5 minutes to obtain a homogeneous solution, followed by $^1$H-NMR measurement. Subsequently 1,1,3,3-tetramethyldisiloxane (177 μl, 1.0 mmol) was added thereto. The mixture was sealed and removed from the glove box, and stirred at 30° C. for 2 hours in an inert gas atmosphere. Two hours later a $^1$H-NMR measurement was conducted and confirmed that the conversion rate of the raw material amide was more than 99%. After the solvent was distilled off, dehydrated pentane was added at 0° C. and stirred for 5 minutes, and then the solvent was distilled off again under reduced pressure to obtain a yellow solid. The obtained yellow solid was brought into a glove box again, dissolved in 5 mL of dehydrated pentane, transferred to a vial tube, allowed to stand in a refrigerator for 12 hours, and the resulting yellow solid was collected by filtration to obtain target substance (I) (20 mg, 13% isolated yield). The resulting product was identified by $^1$H-NMR, $^{13}$C-NMR, IR, HR-MS, and melting point measurement. The results are shown in Table 1 as entry 1.

$^1$H-NMR (CDCl$_3$, 400 MHz): δ2.55 (s, 3H, CH$_3$), 5.58 (d, $J_{H-H}$=13.7 Hz, 1H, —C$\underline{H}$=CH—), 7.07 (d, $J_{H-H}$=7.8 Hz, 4H, o-Ph$^N$), 7.13 (t, $J_{H-H}$=7.8 Hz, 2H, p-Ph$^N$), 7.24 (d, $J_{H-H}$=8.7 Hz, 2H, o-Ph), 7.38 (dd, $J_{H-H}$=7.8 Hz, 4H, m-Ph$^N$), 7.58 (d, $J_{H-H}$=13.7 Hz, 1H, —CH=C$\underline{H}$—), 7.82 (d, $J_{H-H}$=8.7 Hz, 2H, m-Ph).

$^{13}$C$\{^1$H$\}$-NMR (CDCl$_3$, 100 MHz): 26.5, 107.2, 118.0, 124.1, 124.8, 129.2, 129.8, 133.5, 136.1, 143.9, 145.0, 197.4

IR (KBr pellet): ν=1662 (CO) cm$^{-1}$ m.p.: 115-116° C.

HRMS(EI) calcd for C$_{22}$H$_{19}$NO: 313.1467, Found: 313.1466.

[Example 4] Synthesis of N-(2-(4-cyanophenyl)-vinyl)-N,N-diphenylamine (II; R$^1$=CN, R$^2$=H, NAr$_2$=NPh$_2$) Using Iridium Complex B A 10 mL eggplant-shaped flask was charged with a stirrer, 4-cyanophenyl-N,N-diphenylacetamide weighed in an amount of 156 mg (0.5 mmol) and iridium complex B weighed in an amount of 3.5 mg (0.0025 mmol), and a three-way cock was attached thereto. The reaction container was brought into a glove box and further charged with 5 mL of dehydrated toluene and anisole (54 μl, 0.5 mmol) as an internal standard reagent, and stirred for 5 minutes to obtain a homogeneous solution, followed by $^1$H-NMR measurement. Subsequently 1,1,3,3-tetramethyldisiloxane (177 μl, 1.0 mmol) was added thereto. The mixture was sealed and removed from the glove box, and stirred at 30° C. for 1 hour in an inert gas atmosphere. Two hours later a $^1$H-NMR measurement was conducted and confirmed that the conversion rate of the raw material amide was more than 99%. After the solvent was distilled off, heating was conducted at 110° C. for 1 hour. The resulting yellow solid was rinsed with 5 mL of dehydrated pentane thereby obtaining target substance (II) as a yellow solid (107 mg, 0.70 mmol, 40% isolated yield). The resulting product was identified by $^1$H-NMR, $^{13}$C-NMR, IR, HR-MS, and melting point measurement. The results are shown in Table 1 as entry 2.

$^1$H-NMR (CDCl$_3$, 400 MHz): δ5.52 (d, $J_{H-H}$=14.2 Hz, 1H, —C$\underline{H}$=CH—), 7.11 (d, $J_{H-H}$=7.3 Hz, 4H, o-Ph$^N$), 7.19 (t, $J_{H-H}$=7.3 Hz, 2H, p-Ph$^N$), 7.22 (d, $J_{H-H}$=8.7 Hz, 2H, o-Ph), 7.38 (dd, $J_{H-H}$=7.3 Hz, 4H, m-Ph$^N$), 7.47 (d, $J_{H-H}$=8.7 Hz, 2H, m-Ph), 7.53 (d, $J_{H-H}$=14.2 Hz, 1H, —CH=C$\underline{H}$—).

$^{13}$C$\{^1$H$\}$-NMR (CDCl$_3$, 100 MHz): 106.3, 107.0, 119.9, 124.1, 124.44, 125.0, 129.9, 132.5, 136.6, 143.6, 144.8.

IR (KBr pellet): ν=1583(CO) cm$^{-1}$ m.p.: 113-114° C.

HRMS(EI) calcd for C$_{21}$H$_{16}$N$_2$: 296.1313, Found: 296.1313.

[Example 5] Synthesis of N-(2-(4-nitrophenyl)-vinyl)-N,N-diphenylamine (III; R$^1$=NO$_2$, R$^2$=H, NAr$_2$=NPh$_2$) Using Iridium Complex B A 10 mL eggplant-shaped flask was charged with a stirrer, 4-nitrophenyl-N,N-diphenylacetamide weighed in an amount of 166 mg (0.5 mmol) and iridium complex B weighed in an amount of 3.5 mg (0.0025 mmol), and a three-way cock was attached thereto. The reaction container was brought into a glove box and further charged with 5 mL of dehydrated toluene and anisole (54 μl, 0.5 mmol) as an internal standard reagent, and stirred for 5 minutes to obtain a homogeneous solution, followed by $^1$H-NMR measurement. Subsequently 1,1,3,3-tetramethyldisiloxane (177 μl, 1.0 mmol) was added thereto. The mixture was sealed and removed from the glove box, and stirred at 30° C. for 6 hours in an inert gas atmosphere. Six hours later a $^1$H-NMR measurement was conducted and confirmed that the conversion rate of the raw material amide was more than 99%. After the solvent was distilled off, the obtained red viscous solid was dissolved in 5 mL of dehydrated pentane and allowed to stand at −30° C. for 12 hours to obtain target substance (III) as a red solid (97 mg, 0.31 mmol, 61% isolated yield). The resulting product was identified by $^1$H-NMR, $^{13}$C-NMR, IR, HR-MS, and melting point measurement. The results are shown in Table 1 as entry 3.

$^1$H-NMR (CDCl$_3$, 400 MHz): δ5.60 (d, $J_{H-H}$=13.5 Hz, 1H, —CH=CH—), 7.11 (d, $J_{H-H}$=7.7 Hz, 4H, o-Ph$^N$), 7.22 (t, $J_{H-H}$=7.7 Hz, 2H, p-Ph$^N$), 7.30 (d, $J_{H-H}$=8.7 Hz, 2H, o-Ph), 7.43 (dd, $J_{H-H}$=7.7 Hz, 4H, m-Ph$^N$), 7.67 (d, $J_{H-H}$=13.5 Hz, 1H, —CH=CH—), 8.10 (d, $J_{H-H}$=8.7 Hz, 2H, m-Ph).

$^{13}$C{1H}-NMR (CDCl$_3$, 100 MHz): 105.9, 124.0, 124.2, 124.5, 125.3, 129.5, 129.9, 137.6, 144.4, 144.7.

IR (KBr pellet): ν=1575 cm$^{-1}$ m.p.: 150-151° C.

HRMS (EI) calcd for C$_{20}$H$_{16}$N$_2$O$_2$: 316.1212, Found: 316.1211.

[Example 6] Synthesis of N-(2-(4-(benzo[c][1,2,5]thiadiazol-4-yl)phenyl)-vinyl)-N,N-diphenylamine (IV; R$^1$=benzo[c][1,2,5]thiadiazol-4-yl, R$^2$=H, NAr$_2$=NPh$_2$) Using Iridium Complex B A 10 mL eggplant-shaped flask was charged with a stirrer, 4-(benzo[c][1,2,5]thiadiazol-4-yl)-phenyl-N,N-diphenylacetamide weighed in an amount of 211 mg (0.5 mmol) and iridium complex B weighed in an amount of 3.5 mg (0.0025 mmol), and a three-way cock was attached thereto. The reaction container was brought into a glove box and further charged with 5 mL of dehydrated toluene and anisole (54 μl, 0.5 mmol) as an internal standard reagent, and stirred for 5 minutes to obtain a homogeneous solution, followed by $^1$H-NMR measurement. Subsequently 1,1,3,3-tetramethyldisiloxane (177 μl, 1.0 mmol) was added thereto. The mixture was sealed and removed from the glove box, and stirred at 30° C. for 2 hours in an inert gas atmosphere. Two hours later a $^1$H-NMR measurement was conducted and confirmed that the conversion rate of the raw material amide was more than 99%. After the solvent was distilled off, the obtained red viscous solid was dissolved in 5 mL of dehydrated pentane and allowed to stand at −30° C. for 12 hours to obtain target substance (IV) as a red solid (89 mg, 0.21 mmol, 42% isolated yield). The resulting product was identified by $^1$H-NMR, $^{13}$C-NMR, IR, HR-MS, and melting point measurement. The results are shown in Table 1 as entry 4.

$^1$H-NMR (CDCl$_3$, 400 MHz): δ5.69 (d, $J_{H-H}$=14.3 Hz, 1H, —CH=CH—), 7.14-7.17 (m, 6H, Ph), 7.36-7.39 (m, 6H, Ph), 7.50 (d, $J_{H-H}$=14.3 Hz, 1H, —CH=CH—), 7.67 (t, $J_{H-H}$=8.2 Hz, 2H, Ph), 7.85 (d, $J_{H-H}$=8.2 Hz, 2H, Ph), 7.96 (d, $J_{H-H}$=8.2 Hz, 1H, Ph).

$^{13}$C{H}-NMR (CDCl$_3$, 100 MHz): 102.3, 111.5, 112.3, 114.6, 114.9, 115.2, 117.0, 119.0, 119.1, 122.5, 122.9, 123.1, 126.5, 131.7, 140.1

IR (KBr pellet): ν=1632, 1588 cm$^{-1}$ m.p.: 134-135° C.

HRMS(EI) calcd for C$_{26}$H$_{19}$N$_3$S: 405.1300, Found: 405.1300.

[Example 7] Synthesis of N-(2-(4'-nitro-(1,1'-biphenyl)-4-yl)-vinyl)-N,N-diphenylamine (V; R$^1$=Ph-NO, R$^2$=H, NAr$_2$=NPh$_2$) Using Iridium Complex B A 10 mL eggplant-shaped flask was charged with a stirrer, 4'-nitro-(1,1'-biphenyl)-4-yl-N,N-diphenylacetamide weighed in an amount of 204 mg (0.5 mmol) and iridium complex B weighed in an amount of 3.5 mg (0.0025 mmol), and a three-way cock was attached thereto. The reaction container was brought into a glove box and further charged with 5 mL of dehydrated toluene and anisole (54 μl, 0.5 mmol) as an internal standard reagent, and stirred for 5 minutes to obtain a homogeneous solution, followed by $^1$H-NMR measurement. Subsequently 1,1,3,3-tetramethyldisiloxane (177 μl, 1.0 mmol) was added thereto. The mixture was sealed and removed from the glove box, and stirred at 30° C. for 3 hours in an inert gas atmosphere. Three hours later a $^1$H-NMR measurement was conducted and confirmed that the conversion rate of the raw material amide was more than 99%. After the solvent was distilled off, the obtained red viscous solid was dissolved in 5 mL of dehydrated pentane and allowed to stand at −30° C. for 12 hours to obtain target substance (V) as a red solid (115 mg, 0.26 mmol, 59% isolated yield). The resulting product was identified by $^1$H-NMR, $^{13}$C-NMR, IR, HR-MS, and melting point measurement. The results are shown in Table 1 as entry 5.

$^1$H-NMR (CDCl$_3$, 400 MHz): δ5.62 (d, $J_{H-H}$=14.2 Hz, 1H, —CH=CH—), 7.11-7.19 (m, 6H, Ph), 7.31 (d, $J_{H-H}$=8 0.2 Hz, 2H, Ph), 7.35 (dd, $J_{H-H}$=7.7 Hz, 4H, m-Ph), 7.49-7.54 (m, 3H, Ph, —CH=CH—), 7.72 (d, $J_{H-H}$=8.8 Hz, 2H, Ph), 8.27 (d, $J_{H-H}$=8.8 Hz, 2H, Ph).

$^{13}$C{$^1$H}-NMR (CDCl$_3$, 100 MHz): 107.7, 117.9, 121.1, 124.0, 125.1, 127.1, 127.7, 127.9, 128.1, 129.5, 129.8, 130.6, 134.8, 142.3, 142.5, 145.2

IR (KBr pellet): ν=1586, 1552 cm$^{-1}$ m.p.: 194-195° C.

HRMS (EI) calcd for C$_{26}$H$_{20}$N$_2$O$_2$: 392.1525, Found: 392.1525.

[Example 8] Synthesis of N-(2-(4-nitrophenyl)-2-methylvinyl)-N,N-diphenylamine (VI; R=NO$_2$, R$^2$=Me, NAr$_2$=NPh$_2$) Using Iridium Complex B A 20 mL eggplant-shaped flask was charged with a stirrer, 4-nitrophenyl-N,N-diphenylpropanamide weighed in an amount of 693 mg (2.0 mmol) and iridium complex B weighed in an amount of 14.0 mg (0.01 mmol), and a three-way cock was attached thereto. The reaction container was brought into a glove box and further charged with 2 mL of dehydrated toluene and anisole (216 μl, 2.0 mmol) as an internal standard reagent, and stirred for 5 minutes to obtain a homogeneous solution, followed by $^1$H-NMR measurement. Subsequently 1,1,3,3-tetramethyldisiloxane (712 μl, 4.0 mmol) was added thereto. The mixture was sealed and removed from the glove box, and stirred at 30° C. for 30 minutes in an inert gas atmosphere. Thirty minutes later a $^1$H-NMR measurement was conducted and confirmed that the conversion rate of the raw material amide was more than 99%. After the solvent was distilled off, 2 mL of dehydrated toluene was added thereto, heated at 100° C. for 30 minutes and then dried under reduced pressure again. The obtained red viscous liquid was purified twice by silica gel chromatography (hexane, hexane/ethyl acetate=9:1) to obtain target substance (VI) as a red solid (383 mg, 1.16 mmol, 58% isolated yield). The resulting product was identified by $^1$H-NMR, $^{13}$C-NMR, IR, HR-MS, and melting point measurement. The results are shown in Table 1 as entry 6.

$^1$H-NMR (CDCl$_3$, 400 MHz): δ1.68 (d, J$_{H-H}$=1.4 Hz, 3H, —CH═CMe-) 6.82 (q, J$_{H-H}$=1.4 Hz, 1H, —CH═CMe-), 7.06-7.14 (m, 6H, Ph), 7.33 (t, J$_{H-H}$=7 0.3 Hz, 4H, Ph), 7.55 (d, J$_{H-H}$=7.3 Hz, 2H, Ph), 8.16 (d, J$_{H-H}$=7.3 Hz, 2H, Ph).

$^{13}$C{1H}-NMR (CDCl$_3$, 100 MHz): 16.0, 121.0, 122.7, 123.6, 123.9, 125.3, 129.4, 134.4, 145.7, 146.2, 149.1

IR (KBr pellet): ν=1581 cm$^{-1}$ m.p.: 120-121° C.

HRMS (EI) calcd for C$_{21}$H$_{18}$N$_2$O$_2$: 330.1368, Found: 330.1364.

[Example 9] Synthesis of 10-(2-(4-nitrophenyl)-vinyl)-10H-phenoxazine (VII; R$^1$═NO$_2$, R$^2$═H, NAr$_2$=10H-Phenoxazinyl) Using Iridium Complex B A 10 mL eggplant-shaped flask was charged with a stirrer, 10-(4-nitrophenyl)-phenoxazin-10H-ylacetamide weighed in an amount of 173 mg (0.5 mmol) and iridium complex B weighed in an amount of 3.5 mg (0.0025 mmol), and a three-way cock was attached thereto. The reaction container was brought into a glove box and further charged with 1 mL of dehydrated toluene and anisole (54 μl, 0.5 mmol) as an internal standard reagent, and stirred for 5 minutes to obtain a homogeneous solution, followed by $^1$H-NMR measurement. Subsequently 1,1,3,3-tetramethyldisiloxane (177 μl, 1.0 mmol) was added thereto. The mixture was sealed and removed from the glove box, and stirred at 30° C. for 1 hour in an inert gas atmosphere. One hour later a $^1$H-NMR measurement was conducted and confirmed that the conversion rate of the raw material amide was more than 99%. After the solvent was distilled off the solution was heated at 80° C. for 30 minutes, and then the obtained red viscous liquid was dissolved in 10 mL of dehydrated pentane and allowed to stand at −30° C. for 12 hours to obtain a red crystal. Thereafter, the crystal was purified twice by silica gel chromatography (hexane, hexane/ethyl acetate=9:1) to obtain target substance (VII) as a red solid (66 mg, 0.20 mmol, 40% isolated yield). The resulting product was identified by $^1$H-NMR, $^{13}$C-NMR, IR, HR-MS, and melting point measurement. The results are shown in Table 1 as entry 6.

$^1$H-NMR (CDCl$_3$, 400 MHz): δ6.55 (d, J$_{H-H}$=14.6 Hz, 1H, —CH═CH—) 7.00-7.12 (m, 6H, Ph), 7.27 (dd, J$_{H-H}$=8 0.3 Hz, 2H, Ph), 7.34 (d, J$_{H-H}$=8.7 Hz, 2H, Ph), 7.37 (d, J$_{H-H}$=14.6 Hz, 2H, —CH═CH—), 8.13 (d, J$_{H-H}$=8.7 Hz, 2H, Ph).

$^{13}$C{H}-NMR (CDCl$_3$, 100 MHz): 105.1, 117.3, 119.1, 124.0, 124.5, 124.6, 125.4, 131.6, 134.5, 145.0, 145.3, 149.3

IR (KBr pellet): ν=1579 cm$^{-1}$ m.p.: 178-179° C.

HRMS (EI) calcd for C$_{20}$H$_{14}$N$_2$O$_3$: 330.1004, Found: 330.1004.

TABLE 1

| Entry | Compound | R$^1$ | R$^2$ | NAr$_2$ | Ir cat. | time | conv. [%] | $^a$yield [%] |
|---|---|---|---|---|---|---|---|---|
| 1 | (I) | (acetyl group) | H | NPh$_2$ | A | 2 | >99 | 13 |
| 2 | (II) | —CN | H | NPh$_2$ | B | 2 | >99 | 40 |
| 3 | (III) | —NO$_2$ | H | NPh$_2$ | B | 6 | >99 | 61 |
| 4 | (IV) | (benzothiadiazolyl group) | H | NPh$_2$ | B | 2 | >99 | 42 |
| 5 | (V) | (4-nitrophenyl group) | H | NPh$_2$ | B | 3 | >99 | 59 |
| 6 | (VI) | —NO$_2$ | Me | NPh$_2$ | B | 0.5 | >99 | 58 |
| 7 | (VII) | —NO$_2$ | H | (10H-phenoxazinyl) | B | 1 | >99 | 40 |

$^a$Isolated yield [%]

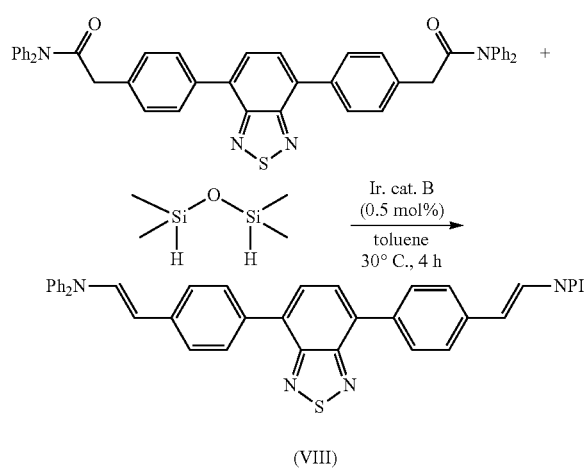

(VIII)

[Example 10] Synthesis of N,N'-((1E,1'E)-(benzo[c][1,2,5]thiadiazole-4,7-diylbis(4,1-phenylene))bis(ethene-2,1-diyl))bis(N-phenylaniline) (VIII) Using Iridium Complex B A 10 mL eggplant-shaped flask was charged with a stirrer, 2,2'-(benzo[c][1,2,5]thiadiazol-4,7-diylbis(4,1-phenylene))bis(N,N'-diphenylacetamide) weighed in an amount of 353 mg (0.5 mmol) and iridium complex B weighed in an amount of 7.1 mg (0.005 mmol), and a three-way cock was attached thereto. The reaction container was brought into a glove box and further charged with 7 mL of dehydrated toluene and anisole (54 µl, 0.5 mmol) as an internal standard reagent, and stirred for 5 minutes to obtain a homogeneous solution, followed by $^1$H-NMR measurement. Subsequently 1,1,3,3-tetramethyldisiloxane (177 µl, 1.0 mmol) was added thereto. The mixture was sealed and removed from the glove box, and stirred at 30° C. for 4 hours in an inert gas atmosphere. Four hours later a $^1$H-NMR measurement was conducted and confirmed that the conversion rate of the raw material amide was more than 99%. After the solvent was distilled off the solution was heated at 80° C. for 30 minutes, and then the obtained red viscous liquid was dissolved in 10 mL of dehydrated pentane and allowed to stand at −30° C. for 12 hours to obtain a red crystal as target substance (VIII) (400 mg, 0.45 mmol, 89% isolated yield). The resulting product was identified by $^1$H-NMR, $^{13}$C-NMR, IR, HR-MS, and melting point measurement.

$^1$H-NMR (CDCl$_3$, 400 MHz): δ5.70 (d, $J_{H-H}$=14.2 Hz, 2H, —CH=CH—), 7.14-7.20 (m, 12H, Ph), 7.30-7.42 (m, 12H, Ph), 7.50 (d, $J_{H-H}$=14.2 Hz, 1H, —CH=CH—), 7.75 (s, 2H, Ph), 7.90 (d, $J_{H-H}$=8.2 Hz, 4H, Ph).

$^{13}$C{H}-NMR (CDCl$_3$, 100 MHz): 108.7, 121.1, 123.9, 124.3, 124.7, 127.5, 129.5, 129.7, 134.3, 138.6, 145.4, 154.3

IR (KBr pellet): ν=1631, 1589 cm$^{-1}$ m.p.: 227-228° C.

HRMS(EI) calcd for C$_{46}$H$_{34}$N$_4$S: 674.2504, Found: 674.2504.

(3) Fluorescent Characteristics of Enamine Compounds (I) to (VIII)

The ultraviolet-visible absorption spectrum was measured at a concentration of 1×10$^{-5}$ M and the fluorescence spectrum was measured at a concentration of 1×10$^{-5}$ M. The solution was prepared as follows. Compounds (I) to (VIII) were dissolved in solvents of differing polarities (hexane, toluene, THF, chloroform, dichloromethane, DMF), respectively, to prepare 1×10$^{-4}$ M solutions. Each 1 mL of the 1×10$^{-4}$ M solution was weighed into a 10 mL volumetric flask using a gas-tight syringe (1 mL), and the corresponding solvents were added to the volumetric flask mark to make a 1×10$^{-5}$ M solution. The 1×10$^{-5}$ M solution was diluted into a 1×10$^{-6}$ M solution in a similar manner. The fluorescent quantum yield was measured at 1×10$^{-5}$ M using an absolute PL quantum yield spectrometer manufactured by Hamamatsu Photonics. The values of the maximum absorption wavelength ($\lambda_{abs}$), the molar absorption coefficient (ε), the excitation wavelength ($\lambda_{ex}$), the maximum fluorescence wavelength ($\lambda_f$) and the fluorescence quantum yield (Φ) of Compounds (I) to (VIII) in various solvents are summarized in Table 2. The absorption spectrum of Compound III is shown in FIG. 1, the fluorescence spectrum of the same is shown in FIG. 2, and the comparative physical properties of the similar structure are shown in FIG. 3. The absorption spectrum and the fluorescence spectrum of Compound (IV) are shown in FIGS. 4 and 5. The absorption spectrum of Compound (VIII) is shown in FIG. 6, and the fluorescence spectrum of the same is shown in FIG. 7.

As is apparent from Table 2 and FIGS. 1 and 2, FIGS. 4 and 5, and FIGS. 6 and 7, the enamine compound according to the present invention exhibits "Solvatochromism" properties in which the maximum absorption wavelength $\lambda_{abs}$ and the maximum fluorescence wavelength $\lambda_f$ change (shift), i.e., the emission color changes depending on the type (polarity) of the solvents.

For example, when the absorption spectrum (FIG. 1) and the fluorescence spectrum (FIG. 2) of Compound (III) of the present invention are examined, the maximum absorption wavelength $\lambda_{abs}$ and the maximum fluorescence wavelength $\lambda_f$ are significantly shifted into the longer wavelength side as the polarity of the solvents become larger (hexane→toluene→THF→CHCl$_3$—CH$_2$Cl$_2$→DMF), and the fluorescence intensities are visually confirmed. Comparing the fluorescence spectra when the solvents are hexane and DMF, the shift amount of the maximum fluorescence wavelength $\lambda_f$ (nm) is as large as 117 nm.

These behaviors were also observed in Compound (IV) and Compound (VIII), and it was found that the compounds of the present invention exhibit very pronounced Solvatochromism properties. As described above, the compound of the present invention enables strong absorption and emission in a wide visible light range, and is suitable for emission in an orange region (from 595 nm to 610 nm) or a red wavelength region (from 610 nm to 750 nm) having high biological tissue permeability, and can be applied to a biological probe, a sensor, or the like. The compound of the present invention can also emit light in the near infrared region on the longer wavelength side by molecular design.

TABLE 2

| Compound | Solvent | $\lambda_{abs}^a$ (nm) | ε | $\lambda_{ex}$ (nm) | $\lambda_f^b$ (nm) | $\Phi^{a,c}$ |
|---|---|---|---|---|---|---|
| (I) | Toluene | 381 | 25,000 | 390 | 433 | 0.01 |
| | THF | 379 | 25,000 | 390 | 428 | 0.02 |
| | | | | | 453 | |
| | | | | | 469 | |
| | CHCl$_3$ | 389 | 32,000 | 390 | 476 | 0.00 |
| | CH$_2$Cl$_2$ | 386 | 44,000 | 390 | 483 | 0.00 |
| | DMF | 388 | 22,000 | 390 | 481 | 0.06 |
| (II) | Toluene | 370 | 31,000 | 370 | 417 | <0.01$^d$ |
| | THF | 370 | 23,800 | 370 | 416 | <0.01$^d$ |
| | | | | | 449 | |
| | | | | | 472 | |

TABLE 2-continued

| Compound | Solvent | $\lambda_{abs}{}^a$ (nm) | ε | $\lambda_{ex}$ (nm) | $\lambda_f{}^b$ (nm) | $\Phi^{a,c}$ |
|---|---|---|---|---|---|---|
| | CHCl$_3$ | 374 | 25,800 | 370 | 418 | <0.01$^d$ |
| | | | | | 443 | |
| | CH$_2$Cl$_2$ | 374 | 22,900 | 370 | 418 | <0.01$^d$ |
| | | | | | 454 | |
| | | | | | 474 | |
| | DMF | 375 | 26,700 | 370 | 415 | <0.01$^d$ |
| | | | | | 453 | |
| (III) | Hexane | 404 | 26,000 | 405 | 474 | 0.02 |
| | Toluene | 424 | 21,700 | 420 | 522 | 0.54 |
| | THF | 431 | 30,200 | 430 | 549 | 0.65 |
| | CHCl$_3$ | 438 | 24,200 | 440 | 576 | 0.09 |
| | CH$_2$Cl$_2$ | 439 | 22,200 | 440 | 586 | 0.05 |
| | DMF | 446 | 22,400 | 445 | 591 | 0.03 |
| (IV) | Hexane | 419 | 10,000 | 430 | 500 | 0.37 |
| | Toluene | 426 | 12,100 | 430 | 552 | 0.61 |
| | THF | 425 | 11,600 | 430 | 589 | 0.26 |
| | CHCl$_3$ | 426 | 11,500 | 430 | 592 | 0.08 |
| | CH$_2$Cl$_2$ | 422 | 9,600 | 430 | 603 | 0.04 |
| | DMF | 422 | 10,000 | 430 | — | 0.01 |
| (V) | Toluene | 413 | 26,000 | 415 | — | 0.64 |
| | THF | 415 | 26,200 | 415 | — | 0.05 |
| | CHCl$_3$ | 419 | 26,000 | — | — | 0.00 |
| | CH$_2$Cl$_2$ | 419 | 22,200 | — | — | 0.00 |
| | DMF | 420 | 25,500 | — | — | 0.00 |
| (VI) | Toluene | 425 | 12,800 | 430 | 562 | 0.13$^d$ |
| | THF | 428 | 14,400 | 430 | 605 | 0.17$^d$ |
| | CHCl$_3$ | 436 | 15,100 | 440 | 675 | 0.01$^d$ |
| | CH$_2$Cl$_2$ | 436 | 14,500 | 440 | — | — |
| | DMF | 435 | 14,200 | 440 | — | — |
| (VII) | Toluene | 431 | 17,000 | 430 | 494 | <0.01$^d$ |
| | THF | 433 | 17,100 | 430 | 493 | <0.01$^d$ |
| | CHCl$_3$ | 442 | 17,300 | 440 | — | — |
| | CH$_2$Cl$_2$ | 440 | 14,600 | 440 | 508 | <0.01$^d$ |
| | DMF | 444 | 13,400 | 440 | — | — |
| (VIII) | Toluene | 464 | 34,300 | 460 | 571 | 0.29 |
| | THF | 465 | 34,100 | 460 | 605 | 0.05 |
| | CHCl$_3$ | 463 | 30,000 | 460 | 602 | 0.31 |
| | CH$_2$Cl$_2$ | 462 | 22,200 | 460 | 613 | 0.17 |
| | DMF | 467 | 22,000 | 460 | — | — |

$^a$at 1.0 × 10$^{-5}$M.
$^b$at 1.0 × 10$^{-6}$M.
$^c$Absolute fluorescence quantum yield.
$^d$Relative to quinine sulfite($\lambda_f$0.55, ex350 nm) in 0.5M sulfuric acid.

(4) Reaction of Hydrosilane with Amide Compound Using Iridium Complex

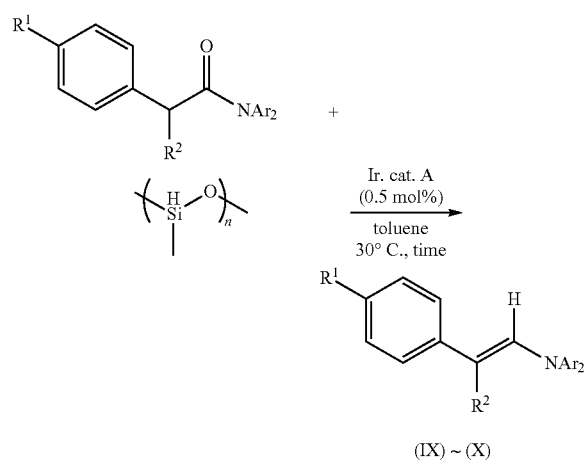

(IX) ~ (X)

[Example 11] Synthesis of N-(2-(4-(dimethylboryl)phenyl)-vinyl)-N,N-diphenylamine (IX; R$^1$=B(mesityl)$_2$, R$^2$=H, NAr$_2$=NPh$_2$) Using Iridium Complex A A 20 mL Schlenk tube degassed/Ar-substituted three or more times was charged with 0.5 mL of dehydrated toluene diluted and adjusted such that [Ir] was 0.5 mol % with respect to the substrate amide, and 4.0 mmol (0.266 g) of polymethylhydrosiloxane (PMHS) in terms of H—Si, and then stirred at room temperature for 30 minutes to prepare a homogeneous solution. The substrate amide in an amount of 1.0 mmol was added thereto and allowed to react for 1 hour at room temperature. After the reaction, the formed insoluble silicon resin was extracted with diethyl ether and passed through a cotton filtration to remove the fine insoluble silicon resin. The solvent was distilled off from the extracted reaction solution under reduced pressure to obtain target compound (IX) (isolated yield: 70%). The resulting product was identified by $^1$H-NMR, IR, HR-MS, and melting point measurement. The results are shown in Table 3 as entry 8.

$^1$H-NMR (CDCl$_3$, 270 MHz): δ2.03 (s, 12H, CH$_3$), 2.30 (s, 6H, CH$_3$), 5.59 (d, J$_{H-H}$=13.9 Hz, 1H, —C$\underline{H}$=CH—), 6.81 (s, 4H, mesityl), 7.05-7.45 (m, 14H, Ph), 7.55 (d, J$_{H-H}$=13.9 Hz, 1H, —CH=C$\underline{H}$—).

IR (KBr pellet): ν=1584 cm$^{-1}$ m.p.: 95-97° C.

HRMS (FAB) calcd for C$_{38}$H$_{38}$NB: 519.3097, Found: 519.3106.

[Example 12] Synthesis of N-(2-(4-(dimethylboryl)phenyl)-vinyl)-N,N-bis(p-methoxyphenyl)amine (X; R$^1$=B(mesityl)$_2$, R$^2$=H, NAr$_2$=N(p-MeOC$_6$H)$_2$) Using Iridium Complex A A 20 mL Schlenk tube degassed/Ar-substituted three or more times was charged with 0.5 mL of dehydrated toluene diluted and adjusted such that [Ir] was 0.5 mol % with respect to the substrate amide, and 4.0 mmol (0.266 g) of polymethylhydrosiloxane (PMHS) in terms of H—Si, and then stirred at room temperature for 30 minutes to prepare a homogeneous solution. The substrate amide in an amount of 1.0 mmol was added thereto and allowed to react for 1 hour at room temperature. After the reaction, the formed insoluble silicon resin was extracted with diethyl ether and passed through a cotton filtration to remove the fine insoluble silicon resin. The solvent was distilled off from the extracted reaction solution under reduced pressure to obtain target compound (X) (isolated yield: 62%). The resulting product was identified by $^1$H-NMR, IR, HR-MS, and melting point measurement. The results are shown in Table 3 as entry 9.

$^1$H-NMR (CDCl$_3$, 270 MHz): δ2.03 (s, 12H, CH$_3$), 2.30 (s, 6H, CH$_3$), 3.81 (s, 6H, OCH$_3$), 5.49 (d, J$_{H-H}$=14.0 Hz, 1H, —C$\underline{H}$=CH—), 6.81 (s, 4H, mesityl), 6.88 (d, J$_{H-H}$=8.7 Hz, 4H, Ar), 7.03 (d, J$_{H-H}$=8 0.7 Hz, 4H, Ar), 7.13 (d, J$_{H-H}$=7.7 Hz, 4H, Ar), 7.38 (d, J$_{H-H}$=7.7 Hz, 4H, Ar), 7.49 (d, J$_{H-H}$=14.0 Hz, 1H, —CH=C$\underline{H}$—).

$^{13}$C{1H}-NMR (CDCl$_3$, 100 MHz): δ21.3, 23.5, 55.6, 106.3, 114.9, 123.4, 125.2, 125.4, 128.1, 128.3, 129.1, 136.4, 137.9, 138.2, 138.7, 140.9, 141.5, 142.0, 1143.0, 156.6

IR (KBr pellet): ν=1585 cm$^{-1}$ m.p.: 100-103° C.

HRMS (FAB) calcd for C$_{40}$H$_{42}$NO$_2$B: 579.3309, Found: 579.3310.

TABLE 3

| Entry | Compound | R[1] | R[2] | NAr2 | Ir cat. | time | conv. [%] | [a]yield [%] |
|---|---|---|---|---|---|---|---|---|
| 8[b] | (IX) | —B(mesityl)$_2$ | H | NPh$_2$ | A | 1 | >99 | 70 |
| 9[b] | (X) | —B(mesityl)$_2$ | H | 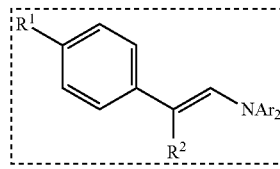 | A | 1 | >99 | 62 |

[a]Isolated yield [%]
[b]polymethylhydrosiloxane (PMHS) was used (5) Fluorescent Characteristics of Enamine Compounds (IX) to (X)

The ultraviolet-visible absorption spectrum was measured at a concentration of $1\times10^{-5}$ M and the fluorescence spectrum was measured at a concentration of $1\times10^{-5}$ M. The solution was prepared as follows. Compounds (IX) to (X) were dissolved in solvents of differing polarities (cyclohexane, ethanol), respectively, to prepare $1\times10^{-4}$ M solutions. Each 1 mL of the $1\times10^{-4}$ M solution was weighed into a 10 mL volumetric flask using a gas-tight syringe (1 mL), and the corresponding solvents were added to the volumetric flask to the volumetric flask mark to make a $1\times10^{-5}$ M solution. The $1\times10^{-5}$ M solution was diluted into a $1\times10^{-6}$ M solution in a similar manner. The fluorescent quantum yield was measured at $1\times10^{-5}$ M. The values of the maximum absorption wavelength ($\lambda_{abs}$), the molar absorption coefficient ($\varepsilon$), the excitation wavelength ($\lambda_{ex}$), the maximum fluorescence wavelength ($\lambda_f$), and the fluorescence quantum yield ($\Phi$) of Compounds (IX) to (X) in various solvents are summarized in Table 4.

TABLE 4

| Compound | Solvent | $\lambda_{abs}{}^a$ (nm) | $\varepsilon$ | $\lambda_{ex}$ (nm) | $\lambda_f{}^b$ (nm) | $\Phi^a$ |
|---|---|---|---|---|---|---|
| (IX) | cyclohexane[c] | 405 | — | 300 | — | 0.03 |
|  | ethanol[d] | 405 | — | 300 | 478 | <0.01 |
| (X) | cyclohexane[c] | 418 | — | 300 | 461 | 0.08 |
|  | ethanol[d] | 418 | — | 300 | 509 | <0.01 |

[a]at $1.0 \times 10^{-5}$M.
[b]at $1.0 \times 10^{-6}$M.
[c]Relative to 9,10-diphenylanthracene.
[d]Relative to anthracene.

(6) Simulation of the Absorption Wavelength of Enamine Compounds by DFT Calculation A software Gaussian09rev.c was used for the calculations. In the structural optimization of the target molecules, B3LYP was adopted as the functional while 6-31G was adopted as the basis function. The absorption wavelength was calculated by TD calculation for the molecular structure obtained by structure optimization. For the TD calculation, B3LYP was adopted as the functional while 6-31G was adopted as the basis function.

The calculated absorption wavelengths, energies (eV) of HOMO and LUMO, and energy differences between the HOMO-LUMO (eV) are listed in Table 5. $R^1$ represents an acceptor site, $R^2$ represents a substituent on an enamine, and NAr$_2$ represents a donor site.

TABLE 5

| Entry | R[1] | R[2] | NAr2 | $\lambda_{abs,calc}$ (nm) | HOMO$_{calc}$ (eV) | LUMO$_{calc}$ (eV) | Eg, calc (eV) |
|---|---|---|---|---|---|---|---|
| 1 | 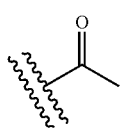 | H | NPh$_2$ | 343 | −5.05 | −1.50 | 3.55 |

TABLE 5-continued

| Entry | R¹ | R² | NAr₂ | $\lambda_{abs,calc}$ (nm) | HOMO$_{calc}$ (eV) | LUMO$_{calc}$ (eV) | Eg, calc (eV) |
|---|---|---|---|---|---|---|---|
| 1 | -CHO (benzaldehyde) | H | NPh₂ | 379 | -5.13 | -1.63 | 3.50 |
| 2 | —CF₃ | H | NPh₂ | 343 | -5.09 | -1.12 | 3.97 |
| 2 | —CN | H | NPh₂ | 360 | -5.21 | -1.49 | 3.72 |
| 3 | —NO₂ | H | NPh₂ | 417 | -5.32 | -2.14 | 3.18 |
| 1 | =C(CN)₂ | H | NPh₂ | 461 | -5.39 | -2.57 | 2.82 |
| 5 | pyridin-4-yl | H | NPh₂ | 373 | -4.96 | -1.30 | 3.66 |
| 5 | thiazolo[5,4-d]thiazol-2-yl | H | NPh₂ | 427 | -4.95 | -1.78 | 3.17 |
| 4 | quinoxalin-5-yl | H | NPh₂ | 486 | -4.79 | -1.87 | 2.92 |
| 4 | benzo[c][1,2,5]thiadiazol-4-yl | H | NPh₂ | 547 | -4.84 | -2.24 | 2.60 |
| 4 | benzo[c][1,2,5]thiadiazol-4-yl | Me | NPh₂ | 548 | -4.91 | -2.32 | 2.59 |
| 4 | benzo[c][1,2,5]thiadiazol-4-yl | Ph | NPh₂ | 552 | -4.88 | -2.30 | 2.58 |
| 5 | 4-nitrophenyl | H | NPh₂ | 525 | -5.37 | -2.75 | 2.62 |

TABLE 5-continued

[Structure: R¹-substituted phenyl with R² and NAr₂ on vinyl group]

| Entry | R¹ | R² | NAr₂ | $\lambda_{abs,calc}$ (nm) | $HOMO_{calc}$ (eV) | $LUMO_{calc}$ (eV) | Eg, calc (eV) |
|---|---|---|---|---|---|---|---|
| 7 | —NO₂ | H | [phenoxazine] | 534 | −5.49 | −2.89 | 2.60 |
| 7 | —NO₂ | H | [carbazole] | 442 | −5.97 | −2.89 | 3.08 |

(Reaction of Hydrosilane with Amide Compound Using Iridium Complex)

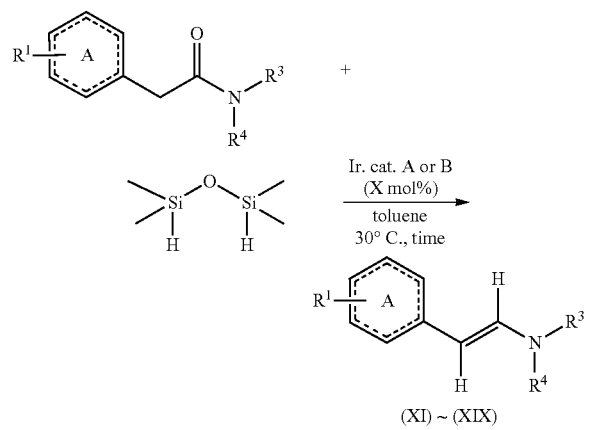

(XI) ~ (XIX)

[Example 13] Synthesis of N-(2-(4-fluorophenyl)-vinyl)-N,N-diphenylamine (XI; R¹=F, A=1,4-C₆H₄, R³=R⁴=Ph) Using Iridium Complex A A 20 mL eggplant-shaped flask was charged with a stirrer and 4-fluorophenyl-N,N-diphenylacetamide weighed out in an amount of 152 mg (0.5 mmol), and a three-way cock was attached thereto. The reaction container was brought into a glove box, and then iridium complex A (0.2 mg, 0.25 μmol), 0.5 mL of dehydrated toluene and anisole (54 μl, 0.5 mmol) as an internal standard reagent were added, and furthermore 1,1,3,3-tetramethyldisiloxane (177 μl, 1.0 mmol) was added thereto. The mixture was sealed and removed from the glove box, and stirred at 30° C. for 2 hours in an inert gas atmosphere. Two hours later a ¹H-NMR measurement was conducted and confirmed that the conversion rate of the raw material amide was 97%. After the solvent was distilled off, the mixture was rinsed with dehydrated pentane at −78° C. and dried under reduced pressure again to obtain target substance (XI) as a white solid (132 mg, 91% isolated yield). The resulting product was identified by ¹H-NMR measurement. The results are shown in Table 6 as entry 1.

¹H-NMR (CDCl₃, 400 MHz): δ5.57 (d, $J_{H-H}$=13.7 Hz, 1H, —C$\underline{H}$=CH—), 6.93 (t, $J_{H-H}$=7.8 Hz, 2H, p-Ph$^N$), 7.09-7.16 (8H, o-Ph$^N$, F-P$\underline{h}$), 7.32 (d, $J_{H-H}$=13.7 Hz, 1H, —CH=C$\underline{H}$—), 7.35 (dd, $J_{H-H}$=7.8 Hz, 4H, m-Ph$^N$).

[Example 14] Synthesis of N-(2-(4-chlorophenyl)-vinyl)-N,N-diphenylamine (XII; R¹=Cl, A=1,4-C₆H₄, R³=R⁴=Ph) Using Iridium Complex A A 20 mL eggplant-shaped flask was charged with a stirrer and 4-chlorophenyl-N,N-diphenylacetamide weighed out in an amount of 161 mg (0.5 mmol), and a three-way cock was attached thereto. The reaction container was brought into a glove box, and then iridium complex A (0.2 mg, 0.25 μmol), 0.5 mL of dehydrated toluene and anisole (54 μl, 0.5 mmol) as an internal standard reagent were added, and furthermore 1,1,3,3-tetramethyldisiloxane (177 μl, 1.0 mmol) was added thereto. The mixture was sealed and removed from the glove box, and stirred at 30° C. for 2 hours in an inert gas atmosphere. Two hours later a ¹H-NMR measurement was conducted and confirmed that the conversion rate of the raw material amide was 95%. After the solvent was distilled off, the mixture was rinsed with dehydrated pentane at −78° C. and dried under reduced pressure again to obtain target substance (XII) as a white solid (109 mg, 71% isolated yield). The resulting product was identified by ¹H-NMR measurement. The results are shown in Table 6 as entry 2.

¹H-NMR (CDCl₃, 400 MHz): δ5.53 (d, $J_{H-H}$=13.7 Hz, 1H, —C$\underline{H}$=CH—), 7.09-7.19 (10H, o-Ph$^N$, p-Ph$^N$, Cl-Ph), 7.35 (dd, $J_{H-H}$=7.8 Hz, 4H, m-Ph$^N$), 7.36 (d, $J_{H-H}$=13.7 Hz, 1H, —CH=C$\underline{H}$—).

[Example 15] Synthesis of N-(2-(4-bromophenyl)-vinyl)-N,N-diphenylamine (XIII; R¹=Cl, A=1,4-C₆H₄, R³=R⁴=Ph) Using Iridium Complex A A 20 mL eggplant-shaped flask was charged with a stirrer and 4-bromophenyl-N,N-diphenylacetamide weighed out in an amount of 183 mg (0.5 mmol), and a three-way cock was attached thereto. The reaction container was brought into a glove box, and then iridium complex B (0.2 mg, 0.15 μmol), 0.5 mL of dehydrated toluene and anisole (54 μl, 0.5 mmol) as an internal standard reagent were added, and furthermore 1,1,3,3-tetramethyldisiloxane (177 μl, 1.0 mmol) was added thereto. The mixture was sealed and removed from the glove box, and stirred at 30° C. for 2 hours in an inert gas atmosphere. Two hours later a 1H-NMR measurement was conducted and confirmed that the conversion rate of the raw material amide was 99% or more. After the solvent was distilled off, the mixture was rinsed with dehydrated pentane at −78° C. and dried under reduced pressure again to obtain target substance (XIII) as a white solid (144 mg, 82% isolated yield). The resulting product was identified by ¹H-NMR measurement. The results are shown in Table 6 as entry 3.

¹H-NMR (CDCl₃, 400 MHz): δ5.50 (d, $J_{H-H}$=13.7 Hz, 1H, —C$\underline{H}$=CH—), 7.08-7.16 (8H, o-Ph$^N$, p-Ph$^N$, Br-Ph), 7.33 (dd, $J_{H-H}$=7.8 Hz, 4H, m-Ph$^N$), 7.35 (d, $J_{H-H}$=7 0.8 Hz, 2H, Br-Ph), 7.38 (d, $J_{H-H}$=13.7 Hz, 1H, —CH=C$\underline{H}$—).

[Example 16] Synthesis of N-(2-(4-formylphenyl)-vinyl)-N,N-diphenylamine (XIV; R¹=CHO, A=1,4-C₆H₄, R³=R⁴=Ph) Using Iridium Complex A A 20 mL eggplant-shaped flask was charged with a stirrer and 4-formylphenyl-N,N-diphenylacetamide weighed out in an amount of 315 mg (1.0 mmol), and a three-way cock was attached thereto. The reaction container was brought into a glove box, and then iridium complex A (78 μg, 0.0 μmol), 0.5 mL of dehydrated toluene and anisole (108 μl, 1.0 mmol) as an internal standard reagent were added, and furthermore 1,1,3,3-tetramethyldisiloxane (353 μl, 2.0 mmol) was added thereto. The mixture was sealed and removed from the glove box, and stirred at room temperature for 2 hours in an inert gas atmosphere. Two hours later a ¹H-NMR measurement was conducted and confirmed that the conversion rate of the raw material amide was 99% or more. After the solvent was distilled off, the mixture was rinsed with dehydrated pentane at −78° C. and dried under reduced pressure again to obtain target substance (XIV) as a white viscous solid (242 mg, 81% isolated yield). The resulting product was identified by ¹H-NMR measurement. The results are shown in Table 6 as entry 4.

¹H-NMR (CDCl₃, 400 MHz): δ5.81 (d, $J_{H-H}$=13.7 Hz, 1H, —C$\underline{H}$=CH—), 7.23 (d, $J_{H-H}$=7.6 Hz, 4H, o-Ph$^N$), 7.25 (d, $J_{H-H}$=8.2 Hz, 2H, CHO-Ph), 7.36-7.46 (6H, m-Ph$^N$, p-Ph$^N$), 7.86 (d, $J_{H-H}$=13.7 Hz, 1H, —CH=C$\underline{H}$—), 8.06 (d, $J_{H-H}$=8.2 Hz, 2H, CHO-Ph), 10.11 (s, 1H, CHO).

[Example 17] Synthesis of N-(2-(3-nitrophenyl)-vinyl)-N,N-diphenylamine (XV; R¹=NO₂, A=1,3-C₆H₄, R³=R⁴=Ph) Using Iridium Complex B A 20 mL eggplant-shaped flask was charged with a stirrer and 3-nitrophenyl-N,N-diphenylacetamide weighed out in an amount of 332 mg (1.0 mmol), and a three-way cock was attached thereto. The reaction container was brought into a glove box, and then iridium complex B (7.1 mg, 0.005 mmol), 0.5 mL of dehydrated toluene and anisole (108 μl, 1.0 mmol) as an internal standard reagent were added, and furthermore 1,1,3,3-tetramethyldisiloxane (353 μl, 2.0 mmol) was added thereto. The mixture was sealed and removed from the glove box, and stirred at 30° C. for 2 hours in an inert gas atmosphere. Two hours later a ¹H-NMR measurement was conducted and confirmed that the conversion rate of the raw material amide was 99% or more. After the solvent was distilled off, the mixture was rinsed with dehydrated pentane at −78° C. and dried under reduced pressure again to obtain target substance (XV) as an orange solid (285 mg, 90% isolated yield). The resulting product was identified by ¹H-NMR measurement. The results are shown in Table 6 as entry 5.

¹H-NMR (CDCl₃, 400 MHz): δ5.51 (d, $J_{H-H}$=13.7 Hz, 1H, —C$\underline{H}$=CH—), 6.77 (dd, $J_{H-H}$=7.3 Hz, 1H, NO₂-Ph), 6.87 (d, $J_{H-H}$=8.2 Hz, 1H, NO₂-Ph), 6.98 (d, $J_{H-H}$=7.6 Hz, 4H, o-Ph$^N$), 7.00 (t, $J_{H-H}$=7.6 Hz, 2H, p-Ph$^N$), 7.16 (dd, $J_{H-H}$=7.3, 8.2 Hz, 4H, m-Ph$^N$), 7.30 (d, $J_{H-H}$=13.7 Hz, 1H, —CH=C$\underline{H}$—), 7.75 (d, $J_{H-H}$=8.2 Hz, 1H, NO₂-Ph), 7.97 (s, 1H, NO₂-Ph).

[Example 18] Synthesis of N-(2-(2-nitrophenyl)-vinyl)-N,N-diphenylamine (XVI; R¹=NO₂, A=1,2-C₆H₄, R³=R⁴=Ph) Using Iridium Complex B A 20 mL eggplant-shaped flask was charged with a stirrer and 2-nitrophenyl-N,N-diphenylacetamide weighed out in an amount of 332 mg (1.0 mmol), and a three-way cock was attached thereto. The reaction container was brought into a glove box, and then iridium complex B (7.1 mg, 0.005 mmol), 0.5 mL of dehydrated toluene and anisole (108 μl, 1.0 mmol) as an internal standard reagent were added, and furthermore 1,1,3,3-tetramethyldisiloxane (353 μl, 2.0 mmol) was added thereto. The mixture was sealed and removed from the glove box, and stirred at 30° C. for 2 hours in an inert gas atmosphere. Two hours later a ¹H-NMR measurement was conducted and confirmed that the conversion rate of the raw material amide was 99% or more. After the solvent was distilled off, the mixture was rinsed with dehydrated pentane at −78° C. and dried under reduced pressure again to obtain target substance (XVI) as a red viscous solid (266 mg, 84% isolated yield). The resulting product was identified by ¹H-NMR measurement. The results are shown in Table 6 as entry 6.

¹H-NMR (CDCl₃, 400 MHz): δ6.53 (d, $J_{H-H}$=13.7 Hz, 1H, —C$\underline{H}$=CH—), 6.65 (dd, $J_{H-H}$=7.3 Hz, 1H, NO₂-Ph), 6.96-7.03 (7H, o-Ph$^N$, p-Ph$^N$, NO₂-Ph), 7.13-7.18 (5H, m-Ph$^N$, NO₂-Ph), 7.31 (d, $J_{H-H}$=13.7 Hz, 1H, —CH=C$\underline{H}$—), 7.65 (d, $J_{H-H}$=9.2 Hz, 1H, NO₂-Ph).

[Example 19] Synthesis of N-(2-(4-nitrophenyl)-vinyl)-N,N-di(4-methoxyphenyl)amine (XVII; R¹=NO₂, A=1,4-C₆H₄, R³=R⁴=(4-MeO) C₆H₄) Using Iridium Complex B A 20 mL eggplant-shaped flask was charged with a stirrer and 4-nitrophenyl-N,N-di(4-methoxyphenyl)acetamide weighed out in an amount of 392 mg (1.0 mmol), and a three-way cock was attached thereto. The reaction container was brought into a glove box, and then iridium complex B (7.1 mg, 0.005 mmol), 0.5 mL of dehydrated toluene and anisole (108 μl, 1.0 mmol) as an internal standard reagent were added, and furthermore 1,1,3,3-tetramethyldisiloxane (353 μl, 2.0 mmol) was added thereto. The mixture was sealed and removed from the glove box, and stirred at 30° C. for 2 hours in an inert gas atmosphere. Two hours later a $^1$H-NMR measurement was conducted and confirmed that the conversion rate of the raw material amide was 99% or more. After the solvent was distilled off, the mixture was rinsed with dehydrated pentane at −78° C. and dried under reduced pressure again to obtain target substance (XVII) as a deep red solid (237 mg, 63% isolated yield). The resulting product was identified by $^1$H-NMR measurement. The results are shown in Table 6 as entry 7.

$^1$H-NMR (CDCl$_3$, 400 MHz): δ3.83 (s, 6H, OMe), 5.86 (d, $J_{H-H}$=13.7 Hz, 1H, —CH=CH—), 6.91 (d, $J_{H-H}$=8.7 Hz, 4H, Ar$^N$), 7.04 (d, $J_{H-H}$=8.7 Hz, 4H, Ar$^N$), 7.19 (d, $J_{H-H}$=8.7 Hz, 2H, NO$_2$-Ph), 7.55 (d, $J_{H-H}$=13.7 Hz, 1H, —CH=CH—), 8.05 (d, $J_{H-H}$=8.7 Hz, 2H, NO$_2$-Ph).

[Example 20] Synthesis of N-(2-(4-(benzo[c][1,2,5]thiadiazol-4-yl)thiophenyl)-vinyl)-N,N-diphenylamine (XVIII; R$^1$=benzo[c][1,2,5]thiadiazol-4-yl, A=2,5-SC$_4$H$_2$, R$^3$=R$^4$=Ph) Using Iridium Complex B A 10 mL eggplant-shaped flask was charged with a stirrer and 4-(benzo[c][1,2,5]thiadiazol-4-yl)-thiophenyl-N,N-diphenylacetamide weighed out in an amount of 428 mg (1.0 mmol) and iridium complex B (7.1 mg, 0.0025 mmol), and a three-way cock was attached thereto. The reaction container was brought into a glove box, and 0.5 mL of dehydrated toluene and anisole (108 μl, 1.0 mmol) as an internal standard reagent were added, and furthermore 1,1,3,3-tetramethyldisiloxane (353 μl, 2.0 mmol) was added thereto. The mixture was sealed and removed from the glove box, and stirred at 30° C. for 2 hours in an inert gas atmosphere. Two hours later a $^1$H-NMR measurement was conducted and confirmed that the conversion rate of the raw material amide was 99% or more. After the solvent was distilled off, the mixture was rinsed with dehydrated pentane at −78° C. and dried under reduced pressure again to obtain target substance (XVIII) as a deep red solid (288 mg, 70% isolated yield). The resulting product was identified by $^1$H-NMR measurement. The results are shown in Table 6 as entry 8.

$^1$H-NMR (CDCl$_3$, 400 MHz): δ5.77 (d, $J_{H-H}$=13.7 Hz, 1H, —CH=CH—), 6.74 (d, $J_{H-H}$=3.7 Hz, 1H, SC$_4$H$_2$), 7.13 (d, $J_{H-H}$=8.7 hz, 4H, o-Ph$^N$, 7.17 (t, $J_{H-H}$=7.3 hz, 2H, p-Ph$^N$), 7.38 (dd, $J_{H-H}$=8.7, 7.3 hz, 4H, m-Ph$^N$), 7.45 (d, $J_{H-H}$=13.7 hz, 1H, —CH=CH—), 7.57 (dd, $J_{H-H}$=6.7, 8.7 hz, 1H, benzodiazol-4-yl), 7.74 (d, $J_{H-H}$=6.7 hz, 1H, benzotiazol-4-yl), 7.83 (d, $J_{H-H}$=8.7 hz, 1H, benzotiazol-4-yl), 7.98 (d, $J_{H-H}$=3.7 Hz, 1H, SC$_4$H$_2$).

TABLE 6

| Entry | Compound | R$^1$ | —A— | R$^3$, R$^4$ | Ir cat. | time | conv. [%] | $^a$yield [%] |
|---|---|---|---|---|---|---|---|---|
| 1 | (XI) | —F | *phenylene* | Ph | A | 2 | 97 | 91 |
| 2 | (XII) | —Cl | *phenylene* | Ph | A | 2 | 95 | 71 |
| 3 | (XIII) | —Br | *phenylene* | Ph | B | 2 | >99 | 82 |
| 4 | (XIV) | —C(=O)H | *phenylene* | Ph | A | 2 | >99 | 81 |
| 5 | (XV) | —NO$_2$ | *meta-phenylene* | Ph | B | 2 | >99 | 90 |
| 6 | (XVI) | —NO$_2$ | *ortho-phenylene* | Ph | B | 2 | >99 | 84 |
| 7 | (XVII) | —NO$_2$ | *phenylene* | *phenylene-OMe* | B | 2 | >99 | 63 |

TABLE 6-continued

| Entry | Compound | R¹ | —A— | R³, R⁴ | Ir cat. | time | conv. [%] | yield[a] [%] |
|---|---|---|---|---|---|---|---|---|
| 8 | (XVIII) | (benzothiadiazole) | (thiophene) | Ph | B | 4 | >99 | 70 |

[a]Isolated yield [%]

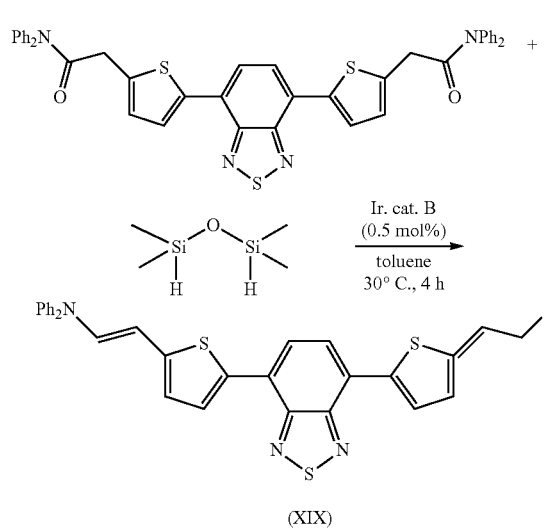

(XIX)

[Example 21] Synthesis of N,N'-((1E,1'E)-(benzo[c][1,2,5]thiadiazole-4,7-diylbis(4,1-thiophenylene)))bis(ethene-2,1-diyl)bis(N-phenylaniline) (XIX) Using Iridium Complex B A 10 mL eggplant-shaped flask was charged with a stirrer and 2,2'-(benzo[c][1,2,5]thiadiazol-4,7-diylbis(4,1-thiophenylene))bis(N,N'-diphenylacetamide) weighed out in an amount of 71.8 mg (0.1 mmol) and iridium complex B (0.7 mg, 0.5 μmol), and a three-way cock was attached thereto. The reaction container was brought into a glove box, and 0.5 mL of dehydrated toluene and anisole (54 μl, 0.5 mmol) as an internal standard reagent were added, stirred for 5 minutes to obtain a homogeneous solution, followed by a ¹H-NMR measurement. Thereafter 1,1,3,3-tetramethyldisiloxane (36 μl, 0.1 mmol) was added to the mixture and sealed and removed from the glove box, and stirred at 30° C. for 4 hours in an inert gas atmosphere. Four hours later a ¹H-NMR measurement was conducted and confirmed that the conversion rate of the raw material amide was 99% or more. After the solvent was distilled off, the mixture was rinsed with dehydrated pentane at −78° C. and dried under reduced pressure again to obtain target substance (XIX) as a deep red solid (41 mg, 60% isolated yield). The resulting product was identified by ¹H-NMR measurement.

¹H-NMR (CDCl₃, 400 MHz): δ5.78 (d, $J_{H-H}$=13.7 Hz, 2H, —C$\underline{H}$=CH—), 6.72 (d, $J_{H-H}$=3.7 Hz, 2H, SC₄$\underline{H}_2$), 7.13 (d, JH-H=8.7 Hz, 8H, o-Ph$^N$), 7.17 (t, JH-H=7.3 Hz, 4H, p-Ph$^N$), 7.38 (dd, $J_{H-H}$=8.7, 7.3 Hz, 8H, m-Ph$^N$), 7.45 (d, $J_{H-H}$=13.7 Hz, 2H, —CH=C$\underline{H}$—), 7.74 (s, 2H, benzothiadiazol-4-yl), 7.96 (d, $J_{H-H}$=3.7 Hz, 2H, SC₄$\underline{H}_2$)

(Ultraviolet-visible Light Absorption and Fluorescent Characteristics of Enamine Compounds (XI) to (XIX))

Example 22

The ultraviolet-visible absorption spectrum was measured at a concentration of 1×10⁻⁵ M and the fluorescence spectrum was measured at a concentration of 1×10⁻⁵ M. For each measurement, an ultraviolet-visible absorption wavelength measurement device and a fluorescence emission wavelength measurement device manufactured by JASCO Corporation were used. The solution was prepared as follows. Compounds (XI) to (XIX) were dissolved in solvents of differing polarities (hexane, toluene, THF), respectively, to prepare 1×10⁻⁴ M solutions. Each 1 mL of the 1×10⁻⁴ M solution was weighed into a 10 mL volumetric flask using a gas-tight syringe (1 mL), and the corresponding solvents were added to the volumetric flask mark to make a 1×10⁻⁵ M solution. The values of the maximum absorption wavelength ($\lambda_{abs}$), the molar absorption coefficient (ε), the excitation wavelength ($\lambda_{ex}$), the maximum fluorescence wavelength ($\lambda_f$), and the fluorescence quantum yield (Φ) of Compounds (XI) to (XIX) in various solvents are summarized in Table 7.

TABLE 7

| Compound | Solvent | $\lambda_{abs}$[a] (nm) | ε | $\lambda_{ex}$ (nm) | $\lambda_f^a$ (nm) | Φ[b] |
|---|---|---|---|---|---|---|
| (XI) | CH₂Cl₂ | 310 | 2,100 | 310 | 398 | <0.01 |
| (XII) | CH₂Cl₂ | 344 | 2,500 | 340 | 411 | <0.01 |
| (XIII) | CH₂Cl₂ | 347 | 2,900 | 350 | 414 | <0.01 |
| (XIV) | Hexane | 381 | 5,700 | 380 | 426 | <0.01 |
|  | Toluene | 391 | 6,200 | 390 | 451 | 0.01 |
|  |  |  |  |  | 469 |  |
|  | THF | 392 | 1,800 | 390 | 455 | 0.02 |
|  |  |  |  |  | 473 |  |
| (XV) | Hexane | 335 | 17,700 | 335 | 492 | <0.01 |
|  | Toluene | 341 | 34,200 | 340 | 589 | <0.01 |
|  | THF | 341 | 29,300 | 340 | 662 | <0.01 |
| (XVI) | Hexane | 405 | 8,800 | 405 | 517 | <0.01 |
|  | Toluene | 424 | 9,100 | 420 | 565 | <0.01 |
|  | THF | 426 | 6,500 | 425 | 579 | <0.01 |
| (XVII) | Hexane | 422 | 3,000 | 420 | 508 | 0.15 |
|  | Toluene | 445 | 18,200 | 445 | 574 | 0.12 |
|  | THF | 452 | 21,000 | 450 | 633 | <0.01 |
| (XVIII) | Hexane | 484 | 14,100 | 480 | 586 | 0.22 |
|  | Toluene | 492 | 18,800 | 490 | 637 | 0.19 |
|  | THF | 492 | 13,600 | 490 | 708 | 0.11 |
| (XIX) | Hexane | 563 | 4,600 | 560 | 665 | 0.91 |
|  | Toluene | 566 | 9,900 | 560 | 731 | 0.53 |
|  | THF | 572 | 7,600 | 570 | 766 | 0.25 |

[a]at 1.0 × 10⁻⁵M.
[b]Relative to quinine sulfite ($\lambda_f$0.55, ex350 nm) in 0.5M sulfuric acid.

(Solution Luminescence Due to Addition of Reagent to Enamine Compound)

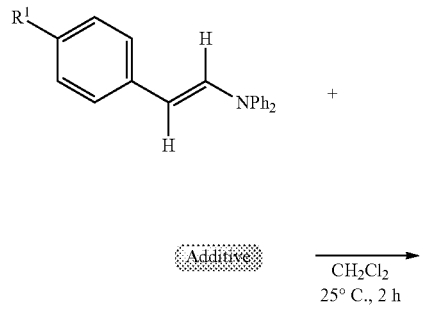

and dehydrated methylene chloride (1 mL) as a solvent and 2-iodo-1,3-dimethyl-1H imidazol-3-ium trifluoromethanesulfonate C (3.7 mg, 0.01 mmol) or tris(pentafluorophenyl)borane D (5.1 mg, 0.01 mmol) or p-toluenesulfonic acid monohydrate E (1.9 mg, 0.01 mmol) as a reagent were added thereto, and the mixture was stirred at room temperature for 2 hours. After the reaction, the solution was irradiated with a UV lamp of 365 nm in a dark room. As a result, the solution luminescence was not exhibited in all enamines having no additive (see Tables 1 and 6), but the solution luminescence was visually confirmed in all the systems to which reagents C, D, and E were added. The solutions were then diluted to $10^{-4}$ M and the UV and fluorescent spectra were measured. In the UV spectrum, a change in the signal depending on the presence or absence of the additive was observed, but no significant signal was obtained in the fluorescence spectrum in all samples. The results of the above 12 samples are summarized in Table 8. The UV spectra for the 12 samples are also shown in FIG. 8.

TABLE 8

| Reagent | Amount (mg) | Enamine Compound | Amount (mg) | UV Spectrum $\lambda_{abs}$ (nm)[a] | $\varepsilon_{max}$ | Fluorescence (visual information) Luminous Intensity[b] | Color |
| --- | --- | --- | --- | --- | --- | --- | --- |
| C | 3.7 | (III) | 3.0 | 374 | 1,500 | A | Blue to Yellow |
| C | 3.0 | (XI) | 2.9 | 295,340 | 2,300 | B | Violet to Blue |
| C | 3.0 | (XII) | 3.1 | 290,338 | 1,900 | B | Blue |
| C | 2.9 | (XIII) | 3.6 | 291,344 | 1,700 | B | Blue |
| D | 2.9 | (III) | 3.0 | 379,427 | 2,000 | B | Yellow |
| D | 2.9 | (XI) | 2.9 | 286,372 | 2,500 | A | Blue |
| D | 3.1 | (XII) | 3.1 | 290,344 | 2,000 | A | Blue |
| D | 3.1 | (XIII) | 3.6 | 270,346 | 1,800 | A | Blue |
| E | 3.1 | (III) | 3.0 | 282,376 | 1,600 | A | Yellow |
| E | 3.6 | (XI) | 2.9 | 285,340 | 2,100 | A | Blue to Green |
| E | 3.6 | (XII) | 3.1 | 283,338 | 2,200 | A | Blue to Green |
| E | 3.6 | (XIII) | 3.6 | 281,340 | 2,400 | A | Blue to Green |

[a] in $CH_2Cl_2$, $1.0 \times 10-4M$.
[b] A: Weak light emitted, B: Strong light emitted

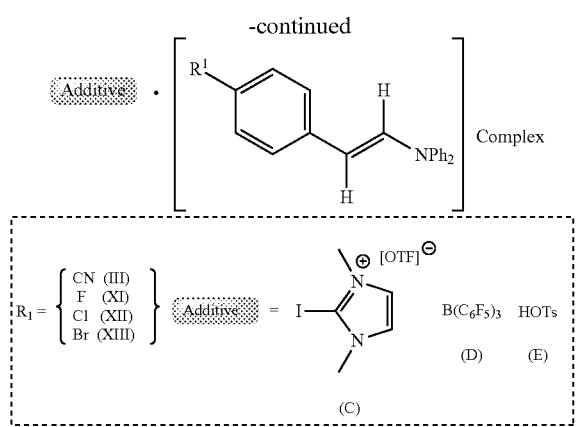

-continued (Solid Luminescence Due to Addition of Reagent to Enamine Compound)

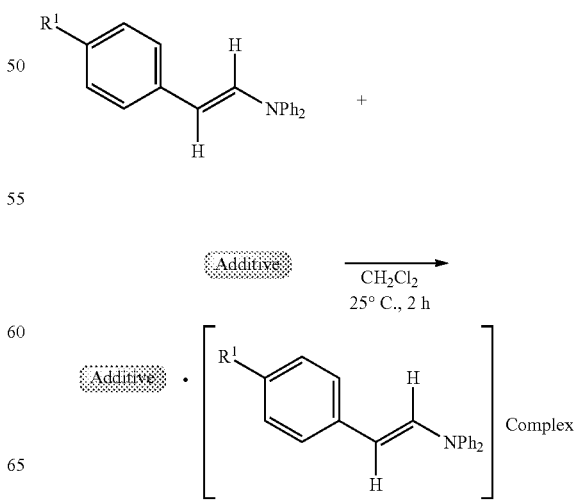

Example 23

A stirrer was placed in a 5 mL screw tube, and 0.01 mmol each of enamine compound (III) or (XI) or (XII) or (XIII) was weighed out. The reactor was brought into a glove box, -continued

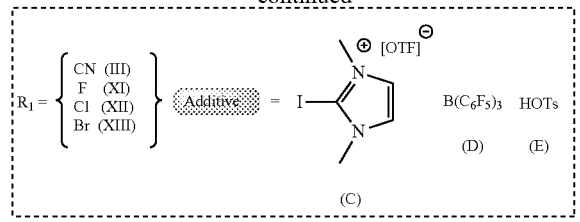

Example 24

A stirrer was placed in a 5 mL screw tube, and 0.01 mmol each of enamine compound (III) or (XI) or (XII) or (XIII) was weighed out. The reactor was brought into a glove box, and dehydrated methylene chloride (1 mL) as a solvent and 2-iodo-1,3-dimethyl-1H imidazol-3-ium trifluoromethanesulfonate C (3.7 mg, 0.01 mmol) or tris(pentafluorophenyl) borane D (5.1 mg, 0.01 mmol) or p-toluenesulfonic acid monohydrate E (1.9 mg, 0.01 mmol) as a reagent were added thereto, and the mixture was stirred at room temperature for 2 hours. After the reaction, the solvent was distilled off to obtain a viscous solid, and the obtained solid was irradiated with a UV lamp of 365 nm in a dark room. As a result, the solid luminescence was not exhibited in all enamines having no additive, but the solid luminescence was visually confirmed in some of the systems to which reagents C, D, and E were added. For the four samples exhibited particularly strong intensities, the absorption wavelength and the fluorescence wavelength of the solid luminescence were measured using a fluorescence measurement device manufactured by Hamamatsu Photonics. The results of the above 12 samples are summarized in Table 9.

TABLE 9

| Reagent | Amount (mg) | Enamine Compound | Amount (mg) | Fluorescence (visual information) | | Fluorescence (measurement) | |
|---|---|---|---|---|---|---|---|
| | | | | Luminous Intensity[b] | Color | Excitation Wavelength | Fluorescence Wavelength |
| C | 3.7 | (III) | 3.0 | A | Yellow | — | — |
| C | 3.0 | (XI) | 2.9 | B | Violet | 370 | 427 |
| C | 3.0 | (XII) | 3.1 | B | Blue | 380 | 445 |
| C | 2.9 | (XIII) | 3.6 | B | Blue | 380 | 449 |
| D | 2.9 | (III) | 3.0 | B | Yellow | 420 | 565 |
| D | 2.9 | (XI) | 2.9 | — | — | — | — |
| D | 3.1 | (XII) | 3.1 | — | — | — | — |
| D | 3.1 | (XIII) | 3.6 | — | — | — | — |
| E | 3.1 | (III) | 3.0 | — | — | — | — |
| E | 3.6 | (XI) | 2.9 | — | — | — | — |
| E | 3.6 | (XII) | 3.1 | — | — | — | — |
| E | 3.6 | (XIII) | 3.6 | — | — | — | — |

[a] in $CH_2Cl_2$, $1.0 \times 10^{-4}$ M.
[b] A: Weak light emitted, B: Strong light emitted

The invention claimed is:

1. An enamine compound of formula (1)

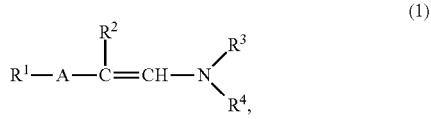

(1)

wherein $R^1$ is a halogen, a nitro group, an acyl group, a cyano group, a hydrocarbon oxycarbonyl group, an unsubstituted carboxamide group, an aromatic heterocyclic group, or $-A^1-C(R^5)=CH-N(R^6)(R^7)$, $A^1$ is a single bond, an unsubstituted divalent aromatic hydrocarbon group, an unsubstituted divalent aromatic heterocyclic group, or an unsubstituted divalent unsaturated aliphatic hydrocarbon group, $R^5$ is H or an unsubstituted hydrocarbon group, $R^6$ and $R^7$ are independently an unsubstituted aromatic hydrocarbon group, or an unsubstituted aromatic heterocyclic group, or $R^6$ and $R^7$ together form a bicyclic aromatic heterocyclic group comprising two or more nitrogen atoms or a nitrogen atom and an oxygen atom or a sulfur atom, or a tricyclic aromatic heterocyclic group, and A is an unsubstituted phenylene group, $R^2$ is H or an unsubstituted hydrocarbon group, and $R^3$ and $R^4$ are each an unsubstituted phenyl group.

2. The enamine compound of claim 1, wherein $R^2$ is H, an aliphatic hydrocarbon group, or an aromatic hydrocarbon group.

3. The enamine compound of claim 1, wherein $R^2$ is H, an alkyl group having 1 to 6 carbon atoms, or an aromatic hydrocarbon group having 6 to 10 carbon atoms.

4. The enamine compound of claim 1, wherein $R^1$ is a halogen atom, a nitro group, an acyl group, a cyano group, a hydrocarbon oxycarbonyl group, a carboxamide group optionally comprising an alkyl group as a substituent, a dicyanoethenyl group, an aromatic heterocyclic group having at least 1 to 4 heteroatoms, or $-A^1-C(R^5)=CH-N(R^6)(R^7)$, wherein $A^1$ is an aromatic heterocyclic group having 1 to 4 heteroatoms, $R^5$ is H or a hydrocarbon group, and $R^6$ and $R^7$ are independently an aromatic hydrocarbon group or an aromatic heterocyclic group, or $R^6$ and $R^7$ together form a bicyclic aromatic heterocyclic group comprising two or more nitrogen atoms or a nitrogen atom and an oxygen atom or a sulfur atom, or a tricyclic aromatic heterocyclic group.

5. A method for producing the enamine compound of claim 1, the method comprising:

reacting an amide compound of formula (a)

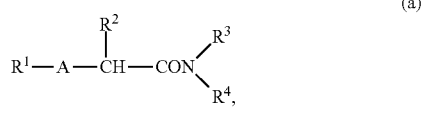

with a hydrosilane compound in the presence of an iridium complex.

6. The method of claim 5, wherein the iridium complex is of formula (3)

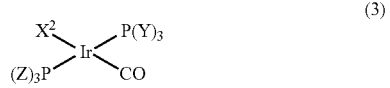

wherein $X^2$ is a halogen atom, and Y and Z each represent a phenyl group, a phenoxy, group, a pyrrolyl group, a perfluorophenoxy group, or a perfluoroalkoxy group.

7. A fluorescent luminescent agent composition, comprising the enamine compound of claim 1.

8. The composition of claim 7, further comprising:
an electron acceptor.

9. The composition of claim 8, wherein the electron acceptor is a cation donor.

10. The composition of claim 9, wherein the cation donor is a proton or a halogen cation.

11. The composition of claim 10, wherein the proton is a Bronsted acid.

12. The composition of claim 10, wherein the halogen cation is a halogen bond donor.

13. The composition of claim 8, wherein the electron acceptor is a Lewis acid.

14. A photosensitizer composition, comprising:
the enamine compound of claim 1.

15. The composition of claim 14, further comprising:
an electron acceptor.

16. The composition of claim 15, wherein the electron acceptor is a cation donor.

17. The composition of claim 16, wherein the cation donor is a proton or a halogen cation.

18. The composition of claim 17, wherein the proton is a Bronsted acid.

19. The composition of claim 17, wherein the halogen cation is a halogen bond donor.

20. The composition of claim 15, wherein the electron acceptor is a Lewis acid.

21. The enamine compound of claim 1, wherein $R^1$ is $-A^1-C(R^5)=CH-N(R^6)(R^7)$.

* * * * *